(12) United States Patent
Habib et al.

(10) Patent No.: US 9,974,751 B2
(45) Date of Patent: *May 22, 2018

(54) ABUSE RESISTANT DRUG FORMULATION

(71) Applicant: CIMA LABS INC., Brooklyn Park, MN (US)

(72) Inventors: Walid Habib, Brooklyn Park, MN (US); Ehab Hamed, Brooklyn Park, MN (US); Derek Moe, Brooklyn Park, MN (US); Carrie Kraling, Brooklyn Park, MN (US); Lisa Hillman, Brooklyn Park, MN (US)

(73) Assignee: Cima Labs Inc., Brooklyn Park, MN (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/731,587

(22) Filed: Dec. 31, 2012

(65) Prior Publication Data

US 2013/0122087 A1 May 16, 2013

Related U.S. Application Data

(60) Division of application No. 13/095,434, filed on Apr. 27, 2011, now abandoned, which is a continuation of application No. 11/900,851, filed on Sep. 13, 2007, now abandoned.

(60) Provisional application No. 60/850,456, filed on Oct. 10, 2006, provisional application No. 60/845,127, filed on Sep. 15, 2006, provisional application No. 60/845,151, filed on Sep. 15, 2006, provisional application No. 60/845,126, filed on Sep. 15, 2006, provisional application No. 60/845,128, filed on Sep. 15, 2006.

(51) Int. Cl.
*A61K 9/20* (2006.01)
*A61K 9/16* (2006.01)
*A61K 9/50* (2006.01)
*A61K 31/485* (2006.01)

(52) U.S. Cl.
CPC .......... *A61K 9/2095* (2013.01); *A61K 9/1652* (2013.01); *A61K 9/1694* (2013.01); *A61K 9/2081* (2013.01); *A61K 9/5047* (2013.01); *A61K 31/485* (2013.01)

(58) Field of Classification Search
None
See application file for complete search history.

(56) References Cited

U.S. PATENT DOCUMENTS

| | | |
|---|---|---|
| 4,814,176 A | 3/1989 | Makino et al. |
| 4,844,909 A | 7/1989 | Goldie et al. |
| 4,861,598 A | 8/1989 | Oshlack |
| 4,863,456 A | 9/1989 | Stephens et al. |
| 4,873,092 A | 10/1989 | Azuma et al. |
| 4,970,075 A | 11/1990 | Oshlack |
| 4,990,341 A | 2/1991 | Goldie et al. |
| 5,133,974 A | 7/1992 | Paradissis et al. |
| 5,169,645 A | 12/1992 | Shukla et al. |
| 5,178,878 A | 1/1993 | Wehling et al. |
| 5,248,669 A * | 9/1993 | Amer .............................. 514/30 |
| 5,266,331 A | 11/1993 | Oshlack et al. |
| 5,273,760 A | 12/1993 | Oshlack et al. |
| 5,286,493 A | 2/1994 | Oshlack et al. |
| 5,321,012 A | 6/1994 | Mayer et al. |
| 5,352,683 A | 10/1994 | Mayer et al. |
| 5,403,593 A | 4/1995 | Royce |
| 5,445,829 A | 8/1995 | Paradissis et al. |
| 5,458,879 A | 10/1995 | Singh et al. |
| 5,460,828 A | 10/1995 | Santus et al. |
| 5,472,712 A | 12/1995 | Oshlack et al. |
| 5,478,577 A | 12/1995 | Sackler et al. |
| 5,500,227 A | 3/1996 | Oshlack et al. |
| 5,503,846 A | 4/1996 | Wehling et al. |
| 5,508,042 A | 4/1996 | Oshlack et al. |
| 5,549,912 A | 8/1996 | Oshlack et al. |

(Continued)

FOREIGN PATENT DOCUMENTS

| | | |
|---|---|---|
| EP | 1419766 | 5/2004 |
| EP | 1504757 | 2/2005 |

(Continued)

OTHER PUBLICATIONS

Mesh to Micron Conversion Chart, http://www.showmegold.org/news/Mesh.htm, retrieved online on Apr. 26, 2016.*
Portenoy et al. "Fentanyl Buccal Tablet (FBT) for Relief of Breakthrough Pain in Opioid-Treated Patients with Chronic Low Back Pain: A Randomized, Placebo-Controlled Study", ASRA 06, Final Abstract, Submitted Aug. 4.
Portenoy et al. "Fentanyl Buccal Tablet (FBT) for Relief of Breakthrough Pain in Opioid-Treated Patients with Chronic Low Back Pain", Current Medical Research and Opinion, vol. 23(7), pp. 223-233, 2007.
Physician's Desk Reference 57th ed. 2003 p. 1184 (package insert information for ACTIQ).

(Continued)

*Primary Examiner* — Jennifer A Berrios

(57) ABSTRACT

A pharmaceutical composition may include a granulate which may include at least one active pharmaceutical ingredient susceptible to abuse by an individual mixed with at least two materials, a first material that is substantially water insoluble and at least partially alcohol soluble and a second material that is substantially alcohol insoluble and at least partially water soluble, wherein the active pharmaceutical ingredient and the two materials are granulated in the presence of water and alcohol. The composition may also include a coating on the granulate exhibiting crush resistance which may have a material that is deposited on the granulate using an alcohol based solvent. The composition further comprises a second particle comprising a fat/wax. The present invention also includes a coated granulate, various dosage forms of the composition, as well as methods of production and tableting.

6 Claims, 9 Drawing Sheets

(56) References Cited

U.S. PATENT DOCUMENTS

| | | |
|---|---|---|
| 5,580,578 A | 12/1996 | Oshlack et al. |
| 5,593,694 A | 1/1997 | Hayashida et al. |
| 5,614,218 A | 3/1997 | Olsson et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,731,006 A | 3/1998 | Akiyama et al. |
| 5,744,166 A | 4/1998 | Illum et al. |
| 5,811,126 A | 9/1998 | Krishnamurthy et al. |
| 5,840,754 A | 11/1998 | Guittard et al. |
| 5,849,240 A | 12/1998 | Miller et al. |
| 5,851,555 A | 12/1998 | Sanghvi et al. |
| 5,858,412 A | 1/1999 | Staniforth et al. |
| 5,891,471 A | 4/1999 | Miller et al. |
| 5,904,927 A | 5/1999 | Amiji |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 5,968,661 A | 10/1999 | Saito et al. |
| 6,024,981 A | 2/2000 | Khankari et al. |
| 6,033,686 A * | 3/2000 | Seth .................. 424/482 |
| 6,039,980 A | 3/2000 | Baichwal |
| 6,103,219 A | 8/2000 | Sherwood et al. |
| 6,103,261 A | 8/2000 | Chasin et al. |
| 6,129,933 A | 10/2000 | Oshlack et al. |
| 6,143,322 A | 11/2000 | Sackler et al. |
| 6,143,353 A | 11/2000 | Oshlack et al. |
| 6,155,423 A | 12/2000 | Katzner et al. |
| 6,159,501 A | 12/2000 | Skinhoj et al. |
| 6,162,467 A | 12/2000 | Miller et al. |
| 6,194,005 B1 | 2/2001 | Farah et al. |
| 6,200,604 B1 | 3/2001 | Pather et al. |
| 6,228,398 B1 | 5/2001 | Devane et al. |
| 6,238,704 B1 | 5/2001 | Suzuki et al. |
| 6,245,351 B1 | 6/2001 | Nara et al. |
| 6,245,357 B1 | 6/2001 | Edgren et al. |
| 6,251,430 B1 * | 6/2001 | Zhang et al. .................. 424/468 |
| 6,261,599 B1 | 7/2001 | Oshlack et al. |
| 6,290,990 B1 | 9/2001 | Grabowski et al. |
| 6,294,195 B1 | 9/2001 | Oshlack et al. |
| 6,309,668 B1 | 10/2001 | Bastin et al. |
| 6,316,031 B1 | 11/2001 | Oshlack et al. |
| 6,335,033 B2 | 1/2002 | Oshlack et al. |
| 6,368,625 B1 | 4/2002 | Siebert et al. |
| 6,375,987 B1 | 4/2002 | Farah et al. |
| 6,387,404 B2 | 5/2002 | Oshlack et al. |
| 6,399,096 B1 | 6/2002 | Miller et al. |
| 6,419,954 B1 | 7/2002 | Chu et al. |
| 6,500,459 B1 | 12/2002 | Chhabra et al. |
| 6,531,151 B1 * | 3/2003 | Besse .................. A61K 9/2054 424/464 |
| 6,534,091 B1 | 3/2003 | Garces Garces et al. |
| 6,572,885 B2 | 6/2003 | Oshlack et al. |
| 6,589,960 B2 | 7/2003 | Harclerode et al. |
| 6,680,071 B1 | 1/2004 | Johnson et al. |
| 6,685,964 B1 | 2/2004 | Bartholomaeus et al. |
| 6,699,502 B1 | 3/2004 | Fanara et al. |
| 6,706,281 B2 | 3/2004 | Oshlack et al. |
| 6,730,321 B2 | 5/2004 | Ting et al. |
| 6,730,325 B2 | 5/2004 | Devane et al. |
| 6,733,783 B2 | 5/2004 | Oshlack et al. |
| 6,733,790 B1 | 5/2004 | Garces Garces et al. |
| 6,743,442 B2 | 6/2004 | Oshlack et al. |
| 6,753,014 B1 | 6/2004 | Sjoblom et al. |
| 6,759,059 B1 | 7/2004 | Pettersson et al. |
| 6,780,504 B2 | 8/2004 | Rupprecht et al. |
| 6,793,936 B2 | 9/2004 | Devane et al. |
| 6,863,901 B2 | 3/2005 | Hirsh et al. |
| 6,902,742 B2 | 6/2005 | Devane et al. |
| 6,905,709 B2 | 6/2005 | Oshlack et al. |
| 7,022,313 B2 | 4/2006 | O'Connor et al. |
| 7,090,867 B2 | 8/2006 | Odidi et al. |
| 7,387,792 B2 | 6/2008 | Hirsh et al. |
| 7,399,488 B2 | 7/2008 | Hirsh et al. |
| 7,514,100 B2 | 4/2009 | Oshlack et al. |
| 7,658,939 B2 | 2/2010 | Oshlack et al. |
| 7,776,314 B2 | 8/2010 | Bartholomäus et al. |
| 2002/0006919 A1 * | 1/2002 | Thosar et al. ................. 514/175 |
| 2002/0044966 A1 | 4/2002 | Bartholomaeus et al. |
| 2002/0110595 A1 | 8/2002 | Chang et al. |
| 2002/0110598 A1 | 8/2002 | Chung et al. |
| 2003/0077297 A1 | 4/2003 | Chen et al. |
| 2003/0180362 A1 | 9/2003 | Park et al. |
| 2003/0190358 A1 | 10/2003 | Oshlack et al. |
| 2004/0009219 A1 | 1/2004 | Odidi et al. |
| 2004/0028735 A1 | 2/2004 | Kositprapa |
| 2004/0052844 A1 * | 3/2004 | Hsiao et al. ................. 424/471 |
| 2004/0096499 A1 | 5/2004 | Vaya et al. |
| 2004/0096500 A1 | 5/2004 | Oshlack et al. |
| 2004/0105887 A1 | 6/2004 | Oshlack et al. |
| 2004/0121001 A1 | 6/2004 | Oshlack et al. |
| 2004/0131552 A1 | 7/2004 | Boehm |
| 2004/0142035 A1 | 7/2004 | Chang et al. |
| 2004/0151791 A1 | 8/2004 | Mayo-Alvarez et al. |
| 2004/0157784 A1 | 8/2004 | Chopdekar et al. |
| 2004/0170680 A1 | 9/2004 | Oshlack et al. |
| 2004/0185098 A1 | 9/2004 | Oshlack et al. |
| 2004/0208930 A1 | 10/2004 | Yoneda et al. |
| 2004/0208936 A1 | 10/2004 | Chorin et al. |
| 2004/0224017 A1 * | 11/2004 | Mulye ......................... 424/468 |
| 2004/0253310 A1 | 12/2004 | Fischer et al. |
| 2005/0020613 A1 * | 1/2005 | Boehm et al. ................. 514/282 |
| 2005/0053656 A1 | 3/2005 | Ping |
| 2005/0074493 A1 | 4/2005 | Mehta et al. |
| 2005/0089568 A1 | 4/2005 | Oshlack et al. |
| 2005/0106249 A1 | 5/2005 | Hwang et al. |
| 2005/0163856 A1 | 7/2005 | Maloney et al. |
| 2005/0165038 A1 | 7/2005 | Gordon |
| 2005/0169989 A1 | 8/2005 | Moe et al. |
| 2005/0169990 A1 | 8/2005 | Kao et al. |
| 2005/0245483 A1 | 11/2005 | Brogmann et al. |
| 2005/0266072 A1 | 12/2005 | Oshlack et al. |
| 2006/0024361 A1 | 2/2006 | Odidi et al. |
| 2006/0104909 A1 | 5/2006 | Vaghefi et al. |
| 2006/0153915 A1 | 7/2006 | Park et al. |
| 2006/0153916 A1 | 7/2006 | Vaya et al. |
| 2006/0165038 A1 | 7/2005 | Gordon |
| 2006/0204573 A1 | 9/2006 | Mulye |
| 2006/0233879 A1 | 10/2006 | Lerner et al. |
| 2006/0233880 A1 | 10/2006 | Lerner et al. |
| 2006/0251721 A1 | 11/2006 | Cruz et al. |
| 2006/0263429 A1 | 11/2006 | Feng |
| 2006/0269604 A1 | 11/2006 | Sackler et al. |
| 2007/0003617 A1 | 1/2007 | Fischer et al. |
| 2007/0020335 A1 | 1/2007 | Chen et al. |
| 2007/0203165 A1 | 8/2007 | Shafer et al. |
| 2007/0212414 A1 | 9/2007 | Baichwal et al. |
| 2007/0231268 A1 | 10/2007 | Emigh et al. |
| 2008/0069891 A1 | 3/2008 | Habib et al. |
| 2009/0238868 A1 | 9/2009 | Mehta |
| 2009/0297617 A1 | 12/2009 | Rariy et al. |
| 2009/0304793 A1 | 12/2009 | Boehm |
| 2009/0317355 A1 | 12/2009 | Roth et al. |
| 2010/0015223 A1 | 1/2010 | Cailly-Dufestel et al. |
| 2010/0098771 A1 | 4/2010 | Mehta |

FOREIGN PATENT DOCUMENTS

| | | |
|---|---|---|
| EP | 1782834 | 5/2007 |
| WO | WO9939698 | 8/1999 |
| WO | WO0236099 | 5/2002 |
| WO | WO02092059 | 11/2002 |
| WO | WO2004026256 | 4/2004 |
| WO | WO2004026262 * | 4/2004 |
| WO | WO2004064807 * | 8/2004 |
| WO | WO2004084865 | 10/2004 |
| WO | WO2004093819 | 11/2004 |
| WO | WO2005099674 | 10/2005 |
| WO | WO2007103293 | 9/2007 |
| WO | WO2008140460 | 11/2008 |

(56) References Cited

FOREIGN PATENT DOCUMENTS

| WO | WO2009036812 | 3/2009 |
|----|--------------|--------|
| WO | WO2009059701 | 5/2009 |
| WO | WO2010033195 | 3/2010 |

OTHER PUBLICATIONS

Brendenberg "New Concepts in Administration of Drugs in Tablet Form: Formulation and Evaluation of a Sublingual Tablet for Rapid Absorption and Presentation of an Individualized Dose Administration System Acta Universitatis Upsaliensis." *Comprehensive Summaries of Uppsala Dissertations from the Faculty of Pharmacy* 287 83 pp. Uppsala ISBN 91-554-5600-6 (2003).

Frohof-Hulsmann et al., "Aqueous Ethyl Cellulose Dispersion Containing Plasticizers of Different Water Solubility and Hydroxypropyl Methyl-Cellulose as Coating Material for Diffusion Pellets II: Properties of Sprayed Films", European Journ. of Pharma and Biopharma., Vo. 48, pp. 67-75, 1999.

Hyppola et al.,"Evaluation of Physical Properties of Plasticized Ethyl Cellulose Films Cast From Ethanol Solution Part I", International Journ. of Pharma., vol. 133, pp. 161-170, 1996.

International Search Report for PCT/US2007/020041, dated Feb. 25, 2008.

Vashi et al., "Clinical Pharmacology and Pharmacokinetics of Once-Daily Hydromorphone Hydrochloride Extended-Release Capsules", J. Clin. Pharmacol., vol. 45, pp. 547-554, 2005.

Webster, "PTI-821: Sustained-Release Oxycodone Using Gel-Cap Technology", Expert Opin. Investig. Drugs, vol. 16(3), pp. 1-8, 2007.

Gustafsson et al., "Characterisation of Particle Properties and Compaction Behaviour of Hydroxypropyl Methylcellulose with Different Degrees of Methoxyl/Hydroxypropl Substitution", EP J. of Pharmaceutical Sci. 9, pp. 171-184, 1999.

Siepmann et al., "A New Model Describing the Swelling and Drug Release Kinetics from Hydroxypropyl Methylcellulose Tablets", J. of Pharmaceutical Sci., vol. 88, No. 1, pp. 65-72, Jan. 1999.

Viriden et al., "Investigation of Critical Polymer Properties for Polymer Release and Swelling of HPMC Matrix Tablets", EP J. Pharmaceutical Sci., 36, pp. 297-309, 2009.

Sung et al., "Effect of Formulation Variables on Drug and Polymer Release from HPMC-Based Matrix Tablets", Int'l J. of Pharmaceutics, vol. 142, pp. 53-60, 1996.

* cited by examiner

ABUSE RESISTANT DRUG FORMULATION

CROSS-REFERENCE TO RELATED APPLICATIONS

This application is a continuation application of U.S. patent application Ser. No. 11/900,851, filed Sep. 13, 2007, which claims the benefit of the filing date of U.S. Provisional Patent Application Nos. 60/845,128 filed Sep. 15, 2006, 60/845,127 filed Sep. 15, 2006, 60/845,126 filed Sep. 15, 2006, 60/845,151 filed Sep. 15, 2006, and 60/850,456 filed Oct. 10, 2006, the disclosures of which are hereby incorporated herein by reference.

BACKGROUND OF THE INVENTION

Some prescription drugs provide a controlled release of the active pharmaceutical ingredient ("API") that they are intended to deliver. Controlled release can be a delayed release such as an enteric release in the intestines. It can be an extended release where release begins immediately or shortly after ingestion and continues, either at a constant rate or in some pattern, over an extended period of time, usually from about 6 to about 24 hours. Often this is accomplished using a controlled release coating. Not only are controlled release dosage forms, and especially extended release dosage forms, convenient for the patients as they can take fewer doses throughout the day, but they also help prevent patients from being exposed to too much of the API thereby potentially suffering side effects. However, drug abusers may be at any one time or over a short period of time frustrated by such coatings for that same reason: they may prevent one from obtaining high initial blood concentrations which can cause the very effect—the "high," that the abuser is seeking to obtain.

Indeed, opioids such as oxycodone, are sometimes available as extended release dosage forms for oral administration. One such product is OXCONTIN® from Purdue Pharma L.P. Once swallowed, these types of tablets slowly release their dose of active ingredient over an extended period, often over 6-24 hours. Such an extended release might be accomplished using a coating of some type over the individual particles of the opioid.

However, people can abuse such tablets, using them as recreational drugs, by circumventing the extended release substructure or feature, in this example, the extended release coating. Indeed, a person can compromise this or some other extended release feature by crushing the dosage form through chewing or other means. This can crush any coating or other controlled release feature thereby allowing the release of a relatively large amount of the opioid sooner than intended into their systems once ingested.

Ways of making a dosage form more crush resistant/abuse resistant include those disclosed in U.S. Patent App. Pub. No. 2006/0104909 and 2006/0193914. Coating pharmaceuticals with various materials to achieve other objectives, such as taste-masking, extended release, easier swallowing, etc. are also known. See, for example, U.S. Pat. Nos. 5,178,878; 5,607,697; 6,024,981; 6,280,770; 6,368,625; 6,692,771; 6,740,341; and 2003/0180362.

Another way to circumvent controlled release coatings is to attempt to dissolve the dosage form in a solvent such as water or ethanol. The latter can be particularly dangerous as many prescription drugs should not be taken with alcohol. Depending upon the coating material used, the ethanol or water may act as a solvent, dissolving or eroding the coating and circumventing the intended controlled release. The resulting material can then be administered generally, orally, or in a syringe by a drug abuser.

There are several techniques which have been developed to deter this type of solvent abuse. One abuse deterrent system for oral opioid compounds is described in U.S. Published Application No. 2006/0177380. This disclosure describes a composition containing a gel forming polymer forming an obstacle to syringe uptake, and nasal/mucosal irritant that causes discomfort when excessive amounts of the active compound are inhaled. Such abuse-deterring systems are designed for the nasal or parenteral abuse routes. See also U.S. Patent App. Pub. Nos. 2006/0193914, 2006/0188447, 2006/0193782, 2006/0204573, 2002/0110595, WO2007/087452A2, U.S. Pat. Nos. 6,607,751 and 7,090,867.

SUMMARY OF THE INVENTION

The present invention can be used in any number of contexts including improving manufacturing, storage, and use of dosage forms. However, one particular benefit that can inure from the use of the present invention is rendering an active pharmaceutical ingredient ("API")-containing particle, a coated particle or a dosage form less capable of being crushed, dissolved, injected or otherwise abused.

Certain drugs, such as, for example, the opioid oxycodone, are administered to patients to reduce pain. Successful pain management in many of these patients requires maintenance of certain blood levels of the opioid throughout the day. One way of obtaining acceptable blood levels, used commonly in the pharmaceutical industry, is providing a dose which contains far more drug than is necessary to obtain the desired blood level. Blood levels shortly after the tablet is ingested reach a maximum or $C_{max}$ in a relatively short time, often within hours of ingestion ($T_{max}$) and thereafter, as the body uses, processes and excretes drug from the blood system, the blood level drops. If the $C_{max}$ attained is sufficiently high, and the body's clearance of the drug is sufficiently slow, the blood levels may not fall to subtherapeutic levels for 4-12 hours or even longer. However, with drugs like oxycodone and indeed for many other drugs, this is an impractical and inefficient dosing system. In addition, there is a risk to the patient in that such high initial API levels can cause significant side effects.

Another method of administering drugs involves the use of an extended release mechanism. An extended release can be achieved in many different ways and there are many different release profiles that can be attained. For exemplification only, a granulate material can be produced with a material that when exposed to the digestive tract, swells with available fluids and either slowly erodes or slows the wetting and diffusion of API drug materials contained within the granulate, thus providing a much lower $C_{max}$ and often a much longer $T_{max}$. Ideally, a zero order release is obtained whereby a constant release rate and a constant blood level is attained throughout an extended period of time often six hours or more, more preferably twelve hours or more, and most preferably over about 24 hours. Not only could this strategy reduce the number of doses that need to be taken in a day, it also may prevent one from being exposed to the side effects which can come from unnecessarily high initial blood levels.

Those who seek to abuse these types of products to "get high" can be frustrated by such extended and indeed other controlled release strategies. These strategies actively prevent one from obtaining high blood levels of the drug which can cause the euphoria or other physiologic effects which they are actually seeking, but which normal patients would consider an undesirable or even dangerous side effect. Such prescription drug abusers have learned to circumvent controlled release mechanisms by various administrative abuse means including simply chewing extended release tablets or crushing them using a mortar and a pestle for injection or the like. This can cause the rupture or otherwise compromise the API particle and/or controlled release coating, exposing more of the API to digestion and absorption more quickly, allowing the abuser to achieve much higher blood levels.

Such abuse can have rather far ranging consequences. First, it facilitates drug abuse by individuals which can lead to significant health consequences and even death for the abuser. The consequences of such abuse reach far beyond the abuser and his or her immediate family. Indeed, they can be societal as well. Useful drugs necessary for cancer patients, patients with post-operative or pre-operative pain, chronic pains from arthritis or back injuries need to have available products to allow them to cope. However, the potential for abuse is a constant concern to regulators and law enforcement as these often prescription drugs may be more freely obtainable than truly illegal illicit substances. There are also the societal problems relating to drug use, which includes the cost of their health care, the cost of their rehabilitation, the increase in crime which may come from supporting their drug habit and the like.

In a first embodiment, the present invention may be a coated granulate, comprising a granulate including at least one active pharmaceutical ingredient susceptible to abuse by an individual in an amount between about 0.1 to about 90 percent by weight of the granulate mixed with at least two materials, a first material that is substantially water insoluble and at least partially alcohol soluble and is present in an amount between about 1 to about 90 percent by weight of the granulate and a second material that is substantially alcohol insoluble and at least partially water soluble and is present in an amount between about 1 and about 90 percent by weight of the granulate, the active pharmaceutical ingredient and the two materials are granulated in the presence of water and alcohol; and a coating on the granulate provided in an amount of between about 20 and about 75 percent by weight of the coated granulate exhibiting crush resistance, wherein the coating may be any material such as, for example, cellulose polymers, methacrylate ester copolymers, methacrylic acid copolymers and shellac, said material deposited on said granulate using an alcohol based solvent.

In another embodiment, the present invention may be a pharmaceutical composition comprising a granulate including at least one active pharmaceutical ingredient susceptible to abuse by an individual in an amount between about 0.1 to about 90 percent by weight of the granulate mixed with at least two materials, a first material that is substantially water insoluble and at least partially alcohol soluble and is present in an amount between about 1 to about 90 percent by weight of the granulate and a second material that is substantially alcohol insoluble and at least partially water soluble and is present in an amount between about 1 and about 90 percent by weight of the granulate, the active pharmaceutical ingredient and the two materials are granulated in the presence of water and alcohol; and a coating on the granulate provided in an amount of between about 20 and about 75 percent by weight of the coated granulate exhibiting crush resistance, wherein the coating may be any material such as, for example, cellulose polymers, methacrylate ester copolymers, methacrylic acid copolymers and shellac, said material deposited on said granulate using an alcohol based solvent; and a fat/wax present in an amount between about 1 to about 50 percent by weight of the pharmaceutical composition.

In yet another embodiment, the present invention may be a pharmaceutical dosage form comprising a granulate which may include an opiate in an amount between about 0.1 to about 90 percent by weight of the granulate mixed with an at least two materials, a first material comprising ethylcellulose present in an amount between about 10 to about 40 percent by weight of the granulate and a second material comprising hydroxypropylmethylcellulose present in an amount between about 20 and about 50 percent by weight of the granulate, wherein the active pharmaceutical ingredient and the two materials are granulated in the presence of water and alcohol, said granulate present in an amount sufficient to provide an effective amount of said opiate; a coating on said granulate provided in an amount of between about 40 and about 60 percent by weight of the coated granulate exhibiting crush resistance, wherein the coating comprises a material selected from the group consisting of cellulose polymers, methacrylate ester copolymers, methacrylic acid copolymers and shellac, said material deposited on said granulate using an alcohol based solvent; a fat/wax present in an amount between about 5 to about 25 percent by weight of the final dosage form; and at least one excipient.

In a further embodiment, the present invention may be a method of making a coated granulate which may include combining an at least one active pharmaceutical ingredient susceptible to abuse by an individual in an amount between about 0.1 to about 90 percent by weight of the granulate mixed with an at least two materials, a first material that is substantially water insoluble and at least partially alcohol soluble and is present in an amount between about 1 to about 90 percent by weight of the granulate and a second material that is substantially alcohol insoluble and at least partially water soluble and is present in an amount between about 1 and about 90 percent by weight of the granulate, wherein the active pharmaceutical ingredient and the two materials are granulated in the presence of water and alcohol, forming a wet granulate; milling and drying the wet granulate to form a granulate comprising an average particle size of about 50 to about 700 um; depositing a coating on said granulate provided in an amount of between about 20 and about 75 percent by weight of the coated granulate exhibiting crush resistance, wherein the coating comprises a material selected from the group consisting of cellulose polymers, methacrylate ester copolymers, methacrylic acid copolymers and shellac, said material deposited on said granulate using an alcohol based solvent; and allowing the coating to dry.

In another embodiment, the present invention may be a method of treating a patient having pain which may include administering a pharmaceutical dosage form such a granulate which may include an opiate in an amount between about 0.1 to about 90 percent by weight of the granulate mixed with an at least two materials, a first material comprising ethylcellulose present in an amount between about 10 to about 40 percent by weight of the granulate and a second material comprising hydroxypropylmethylcellulose present in an amount between about 20 and about 50 percent by weight of the granulate, wherein the active pharmaceutical ingredient and the two materials are granulated in the presence of water and alcohol, said granulate present in an amount sufficient to provide an effective amount of said opiate; a coating on said granulate provided in an amount of between about 40 and about 60 percent by weight of the coated granulate exhibiting crush resistance, wherein the coating comprises a material selected from the group consisting of cellulose polymers, methacrylate ester copolymers, methacrylic acid copolymers and shellac, said material deposited on said granulate using an alcohol based solvent; a fat/wax present in an amount between about 5 to about 25 percent by weight of the final dosage form; and at least one excipient.

In still a further embodiment, the present invention may be a pharmaceutical composition comprising at least one coated first particle comprising at least one API susceptible to administration abuse by an individual mixed with an at least two polymers: a first polymer that is substantially water insoluble and at least partially alcohol soluble and a second polymer that is substantially alcohol insoluble and at least partially water soluble. The coating exhibiting crush resistance may be ethylcellulose deposited from an alcohol containing solvent. The composition exhibits resistance to administration abuse by an individual. Moreover, the composition of this embodiment may further comprise a second particle which may be a fat/wax.

In another embodiment, the present invention may be a pharmaceutical composition comprising at least one coated particle comprising an API susceptible to administration abuse by an individual mixed with at least one polymer dispersed or dissolved in an aqueous alcoholic solvent. The coating, which exhibits crush resistance, is deposited from an alcohol containing solvent.

In a further embodiment, the present invention may be a pharmaceutical composition comprising two particles. The first particle comprises an API on a pharmaceutically effective amount wherein the first particle is coated with a polymer. The second particle comprises a fat/wax material present in an amount sufficient to inhibit administration abuse of the API from the first particle.

In another embodiment, the present invention may be a method of making a pharmaceutically active coated particle. At least the API is combined with an aqueous alcoholic solvent to form a wet granulate. The wet granulate is milled and dried to form a granulate which may have a particle size of about 50 to about 700 um. The granulate may then be coated with one or more coating materials from an alcohol containing solvent. The coating may then be dried.

In an additional embodiment, the present invention may be a method of making a dosage form comprising mixing at least one API in an aqueous alcoholic solvent to form a wet granulate. The wet granulate is then milled and dried to form a granulate which may have a particle size of about 50 to about 700 um. The granulate may then be coated with one or more coating materials from an alcohol containing solvent. The coating may then be dried. The blend, or the coated granulate, may then be compressed to form a tablet which may have a hardness preferably between 10 and 200 Newtons.

In yet another embodiment, the present invention may be a method of administering a pharmaceutical composition comprising administering a tablet that inhibits administration abuse wherein the tablet comprises at least one coated first particle which comprises at least one API susceptible to administration abuse by an individual mixed with at least two polymers: a first polymer that is substantially water insoluble and at least partially alcohol soluble and a second polymer that is substantially alcohol insoluble and at least partially water soluble. The coating exhibiting crush resistance, may contain ethylcellulose deposited from an alcohol containing solvent. The composition exhibits resistance to administration abuse by an individual. The composition is compressed to form a tablet. Moreover, the composition may contain a second particle comprising a fat/wax.

In one embodiment, the present invention is directed to a crush-resistant coating ("CR coating"), which provides increased resistance to possible abuse by crushing the resulting coated particles. In one aspect of this embodiment, there is provided CR coated granulates having a high level of plasticity, and dosage forms containing these particles. In another aspect of this embodiment, the CR coated particles include the CR coating of the invention on any type of API containing particle. In still another aspect of this embodiment, the CR coating coats a granulate and the CR coating provides protection against abuse resistance by solvent exposure and/or injection.

The CR coating comprises a polymer which is applied using an alcohol-based solvent—at least sparingly soluble, preferably freely soluble, in an alcohol based solvent and, at most, sparingly soluble in water. In one embodiment, the CR coating comprises a cellulose polymer material applied with or from an alcohol based solvent (at least about 90% alcohol, not more than about 10% water by volume). In a further embodiment, the cellulose polymer material meeting these criteria is an ethylcellulose. Ethylcellulose, when dissolved or dispersed in an alcohol based solvent as described herein, may impart improved properties, including added crush resistance, in comparison to an identical coating applied using water alone or a high water content solvent (more than 10% water).

Another embodiment of the present invention is a dosage form containing controlled release CR coated particles. The CR coating may provide such controlled release. "Controlled release" encompasses both an extended release which extends and/or patterns the release of the API over time, as well as a delayed release such as an enteric release. In a particularly preferred embodiment, the controlled release CR coated particles, extends the release over a period of about 6 to about 24 hours or delays the release such as by preventing release until the dosage form enters the intestines. The added durability of the CR coating helps prevent the particles from being crushed, thus keeping more of the particles intact and capable of releasing the API in the intended manner. Alternatively, separate coatings or other features (such as a granulate) may provide such controlled release. In a preferred embodiment, the invention is an abuse resistant dosage form comprising controlled release CR coated particles wherein the API is an opioid or is otherwise likely to be abused which could provide plasticity and/or which could provide protection against abuse resistance by solvent exposure and/or injection.

In yet another embodiment, the present invention is a granulate which could include a controlled release binder, any of which may or may not be overcoated with a CR coating including a CR coating of the invention.

Preferably, this granulate, particularly when used in conjunction with a CR coating in accordance with the present invention, can provide additional crush/abuse resistance over and above the use of the coating alone.

In one aspect, the granulate has a relatively high level of polymer providing significant plasticity to the resulting granulate. In particularly preferred embodiments, certain modified celluloses such as ethylcellulose, hydroxypropymethylcellulose (HPMC), hydroxypropylcellulose (HPC) hydroxymethylcellulose (HMC), methylcellulose (MC), hydroxyethylcellulose (HEC), carboxymethylcellulose (CMC), and the like can be granulated with the API to provide a granulate with such plasticity. In one preferred aspect, these modified celluloses are generally water soluble and generally insoluble in short chain normal alcohols such as $C_1$-$C_6$ alcohols. Without wishing to be bound by any particular theory of operation, it is believed that the elastic, plastic or shock absorbent properties that such high plasticity granulates can provide, particularly when used in combination with a CR coating in accordance with the present invention, provide additional crush resistance benefits.

Indeed, it has been observed that where two particles of similar size and identical API are coated with the same CR coating of the present invention, the high plasticity granulates of the present invention can provide a greater improvement in crush resistance than the same coated formulation with a different granulate.

In still another aspect of this embodiment, the granulate includes not only a polymer providing plasticity as described above, but also a polymer which is at least sparingly soluble, preferably, soluble in short chain normal alcohols and generally at most sparingly soluble in water. One such combination is a binder composed of HPMC and ethylcellulose. These granulates may provide some measure of solvent resistance to dissolution of the API and/or the granulates can gel, retarding the ability to inject the API.

More specifically, in accordance with one aspect of this embodiment, the present invention provides a wet granulate comprising: a first material that is at most "slightly soluble" in water but is at least soluble in alcohol, a second material that is at most "slightly soluble" in alcohol but is at least soluble in water, and an API. By "slightly soluble" it is meant that the material is generally soluble in one of the solvents requiring between about 100 and 1000 parts of solvent to solubilize a single part of the material in question. The material may be dissolvable or dispersible in larger volumes. Whether a dosage form including this granulate is dissolved or an attempt is made to dissolve it in a limited volume of solvent so that the resulting solution can be injected (solvent being water, alcohol or a mixture thereof), the result will be a generally noninjectable mass ranging from an insoluble mass, to a gel, to a viscous slurry.

In a particularly preferred and nonlimiting embodiment, the slightly soluble materials gel in the limited volume of solvent. Thus, in this preferred embodiment, the present invention provides a wet granulate comprising a first material that is at most slightly soluble in water but gels in alcohol and a second material that is at most slightly soluble in alcohol but gels in water, as well as the API as described immediately above. These granulates will swell when dissolved in alcohol or water forming a viscous material which will reduce the ability of an abuser to inject the resulting slurry.

In preferred embodiments, in addition to providing solvent abuse resistance as described herein, the granulate made with these two polymers can provide a controlled release of the API, additional crush resistance and/or taste masking. These granulates can be coated with a controlled release and/or CR coating as previously described.

In another embodiment, the present invention provides a dosage form resistant to solvent abuse comprising a dried wet granulate comprising a first material that is at most slightly soluble in water but is at least soluble in alcohol (sometimes referred to herein as the first slightly soluble material), a second material that is at most slightly soluble in alcohol but is at least soluble in water (sometimes referred to herein as the second slightly soluble material), and an API. The dosage form also generally, but not necessarily, includes at least one excipient, and may include a controlled release and/or CR coating.

In a further embodiment, the invention comprises a formulation comprising a combination of two discrete particles: a first particle containing the active ingredient, and a second particle composed of a fat/wax material. The first particle can be any of the granulates and/or CR coated particles described above. The formulation can be used to prepare a dosage form wherein the resultant dosage form may be resistant to chemical tampering, e.g., solvent dose dumping techniques. It is believed that the combination of particles according to the invention produces a barrier relative to the active ingredient-containing particles against solvent access, thereby protecting and preserving the intended controlled release properties of the active particles.

The invention provides a pre-dosage form composition comprising a first particle comprising a pharmaceutically active ingredient; and a second particle comprising a fat/wax material; wherein the first particle is discrete relative to the second particle, and said second particle is present in an amount sufficient to resist solvent-accelerated release of said pharmaceutically active ingredient from the first particle. The API may be a powder or crystal, or may be a granulate or coated granulate resistant to abuse as described herein.

In one embodiment, the first particle comprises oxycodone as the pharmaceutically active ingredient and the first particle is coated with cellulose or a cellulose derivative, and the second particle comprising the fat/wax material comprises glyceryl behenate.

The invention also provides processes for preparing a dosage form. In one embodiment, the process involves providing a granulate and CR coated particle of the invention, mixing same with at least one additional ingredient or excipient, and forming a dosage form, such as a tablet, capsule, caplet, powder or the like therefrom. In another aspect, the process comprises the steps of: preparing a first particle containing a pharmaceutically active ingredient; combining the first particle with a second particle composed of a fat/wax material, the second particle being selected and present in an amount sufficient to resist solvent-accelerated release of the pharmaceutically active ingredient from the resulting dosage form; and compressing the first and second particles so as to form a tablet. In an embodiment, the first particle can be coated prior to combining with the second particle.

Also, the invention provides a dosage form for providing a chemical barrier to control solvent access to a pharmaceutically active ingredient, the dosage form prepared by the process of: providing a first particle containing an API present in a pharmaceutically effective amount within said dosage form; providing a second particle composed of fat/wax material selected and provided in an amount sufficient to resist solvent-accelerated release of the API from the first particle; combining the first particle and second particle to form a mixture; and forming a solid dosage form from the mixture. In one embodiment, the dosage form can be in the form of a compressed tablet.

In another aspect, the invention provides a dosage form for providing a chemical barrier to control solvent access to a pharmaceutically active ingredient, the dosage form is formed using a composition comprising a first particle containing an API present in a pharmaceutically effective amount together with a second particle composed of fat/wax material present in an amount sufficient to resist solvent-accelerated release of the API from the first particle; and a crush resistant component.

In yet another preferred embodiment, the present invention provides a pre-dosage form composition that provides both solvent abuse resistance as well as crush abuse resistance. The composition comprises a first particle comprising an at least one API granulated with at least two polymers, one of which is substantially water insoluble and at least partially alcohol soluble and one of which is substantially alcohol insoluble and at least partially water soluble. The first particle further comprises a crush resistant coating comprising ethylcellulose applied using an alcohol based solvent. The composition further comprises a second particle comprising a fat/wax, preferably glyceryl behenate, and an at least one additional excipient. The excipient may be a filler such as lactose or mannitol. The coating may further comprise magnesium stearate. The dosage form may also include barrier beads.

In an additional embodiment, the present invention comprises a dosage form including an effective amount of API and a plurality of barrier beads to provide the desired crush resistance. The barrier beads are preferably present in an amount of between about 10 and about 90% by weight of the dosage form. Most preferably, the barrier beads are not coated and/or do not include an API. The dosage form also preferably includes at least one excipient. The API containing particles, barrier beads and excipients are intimately mixed to form the dosage form.

In another aspect of this embodiment, the barrier beads are nearly as big, if not bigger, in size than the average particle size of the API containing particles. Indeed, in a particularly preferred aspect, the average particle size of the barrier beads is equal to or larger than the average particle size of the API containing particle. In yet another aspect of this embodiment, the API containing particles are protected particles which may be, amongst other things, controlled release particles, taste masked particles or crush resistant particles.

Further aspects of the present invention include methods of making the granulates, particle mixtures and coated particles described herein and of making dosage forms including same, as well as methods of using the coated particles of the invention and dosage forms including same, particularly to reduce drug abuse.

DETAILED DESCRIPTION

Figure 1:
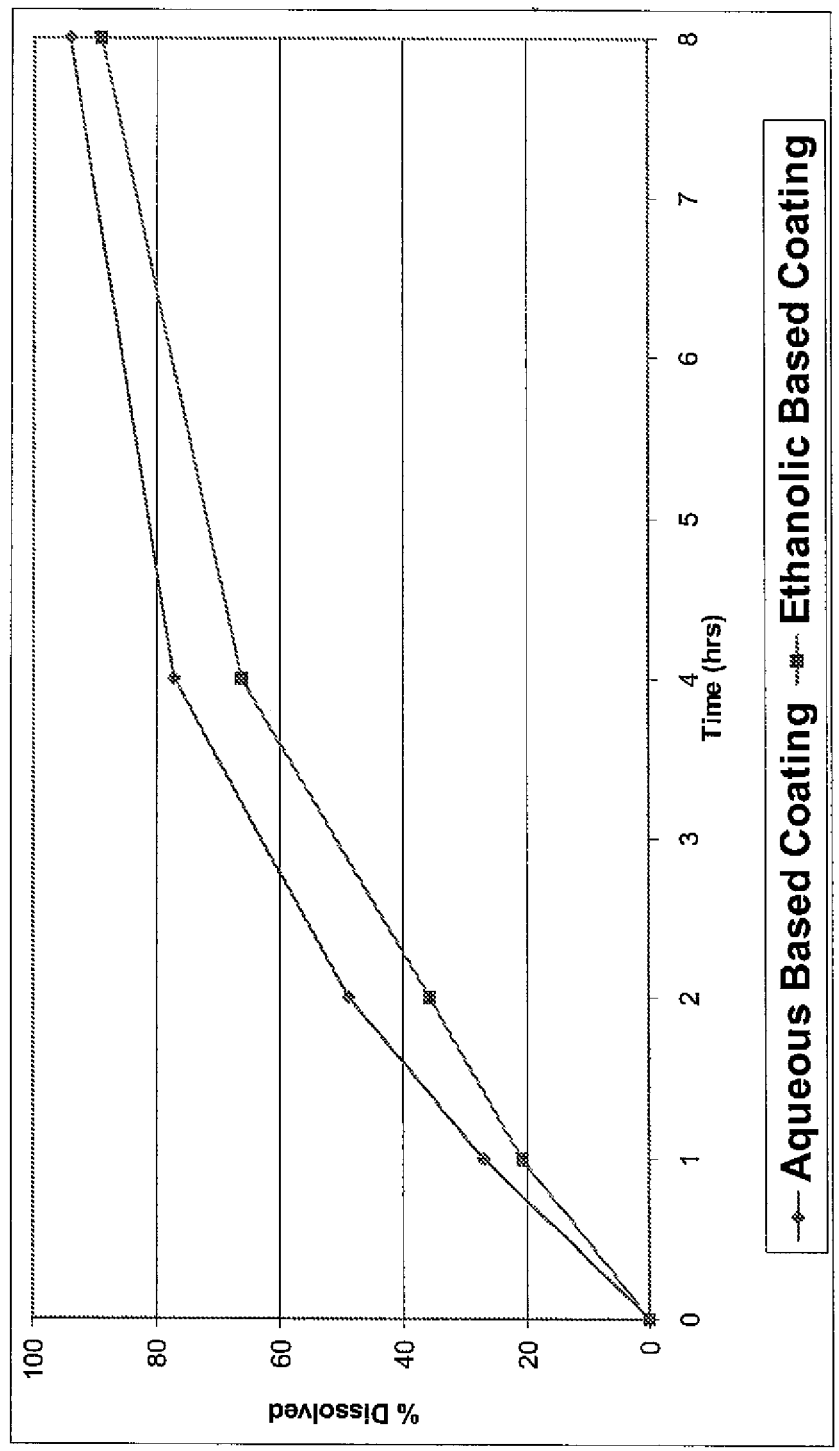
FIG. 1 illustrates comparative dissolution results for granules coated with and without a crush resistant coating in accordance with Examples 1 and 2 of the present invention.

While the specification concludes with the claims particularly pointing and distinctly claiming the invention, it is believed that the present invention will be better understood from the following description. All percentages and ratios used herein are by weight of the total dosage form, or coated particle, as the context requires, unless otherwise designated. All measurements made are at 25° C. and normal pressure unless otherwise designated. All temperatures are in Degrees Celsius unless specified otherwise. The present invention can comprise or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Note that while the specification and claims may refer to a tablet or other dosage form of the invention as, for example, containing particles having a certain particle size or distribution, or a certain type of, for example, nondirect compression sugar, it may be difficult to tell from the final dosage form that the recitation is satisfied. However, such a recitation may be satisfied if the materials used prior to final blending and tablet formulation, for example, meet that recitation. In another example, while it might be difficult to know the weight gain of a coated API-containing granule as it actually exists in a finished tablet, if it is determined that the coated API-containing granulate used to make the tablet, prior to a final blending and compression step, did exhibit the desired coating level, that is sufficient. Indeed, as to any property of a dosage form which cannot be ascertained from the dosage form directly, it is sufficient if that property resides in the formulation just prior to producing a dosage form therefrom.

In a first embodiment, the use of a CR coating in accordance with the present invention can make it more difficult to crush a coated particle and/or circumvent controlled release technologies used, although CR coatings are not limited to situations where abuse is likely. A CR coating of the invention, particularly when used on the granulate described herein, can reduce the degree of crushing of the granulate. Therefore, the structure and desired release rate are preserved, or at least less compromised. The CR coatings of the invention can also be used to overcoat one or more controlled release coatings or structures.

In another embodiment, the CR coating itself also provides a controlled release. As the CR coating should be affected less than a comparable coating from a different solvent system, the length, extent and pattern of release should be closer to that which was intended. A CR coating is therefore particularly useful in connection with the formulation of abuse resistant dosage forms used for analgesia or pain relief such as, for example, opiates, and in particular fentanyl, oxycodone, and the like. The CR coating of the present invention also has advantages in connection with API's that are not likely to be abused, but which may be improperly produced, packaged, shipped or consumed—any place where a compressive force may be applied.

The term "CR coating" means a coating capable of providing some amount of crush resistance to a material coated therewith, applied using an alcohol-based solvent which is a lower chain alcohol $C_1$-$C_7$ including methanol, ethanol, propanol, isopropyl, butanol, tert-butyl alcohol, sec-butyl alcohol, benzyl alcohol, hexanol, cyclohexanol, 1,2 propane diol, 1,3 propane diol, phenol, and the like with no more than about 10% water. The CR coating may impart an added hardness and/or resilience to the API containing particle, retaining more of the intended and desired release of the API, even when stressed by compression or crushing. That does not mean however that the CR coating is, within reason and given the context, unbreakable. Indeed, the CR coating could be pliant and resilient so long as it reduces the incidence of crushing, rupturing, cracking, braking or chipping, and the like.

Crush-resistance of these coatings of the invention can be measured by crushing a defined amount of coated API-containing particles with a mortar and pestle, placing the crushed particle in a solution, such as water, and assaying the resultant solution to determine the amount of API released, compared to that of an identical amount of API-containing particles coated with the same amount of the same coating from a different solvent system. Crush resistant as described herein is defined as the resistance of drug (API) release from the coated particles to enhancement under the influence of mechanical stresses. Drug release from the coated particle is determined in accordance with the methods and apparatus used to measure dissolution and drug release as described in the latest version of United Sates Pharmacopoeia (Chapter <701> 2006), with or without modifications. To assess crushing resistance, drug release from the coated particles is initially measured by placing the particles in a suitable dissolution media in the USP apparatus and measuring how much drug is released over a certain period of time. After subjecting the coated particles to mechanical stresses the drug release from the stressed or tampered protected particles is then measured as described above. The enhancement of release is calculated as the difference in drug release from the coated particles at certain time points before and after applying the mechanical stress. The lower the enhancement the better the crushing resistance. Examples of mechanical stress include, but not limited to, applying compression and/or shear forces onto the particles by using mortar and pestles or any other suitable configuration (ex. pistons and cylinders, ball mills). The severity of stress can be controlled by controlling the force applied, the time period when the particles are exposed to stress (number of hits inflicted by the pestle/piston, duration of running in the mill) and the materials of construction of the mortar and pestle (or any other equipment). For one aspect of this invention, the coated particles were subjected to mechanical stress by using 130 mm OD Porcelain mortar and 1-pound pestle. In summary, the particles were subjected to 12 strokes with the pestle each stroke included a pounding motion followed by a horizontal fully circled abrasive motion. Oxycodone release from the stressed particles was measured in USP Dissolution apparatus 2 using 0.1N HCl as release medium.

The same process can be repeated with comparable particles coated with the same coating material applied using a high water content solvent (greater than 10% by weight) to show how the coating of the invention improves release when compared to other coatings.

Alcohol or alcohol based solvents in accordance with the present invention generally means that the material includes at least about 90% of a $C_1$-$C_7$ alcohol more preferably $C_2$-$C_6$ alcohol and at most about 10% water by volume. More preferably, the alcohol is ethanol which is at least about 95% alcohol by volume with the balance being water. Absolute ethanol may also be used which contains greater than about 99% ethanol by volume. The coating produced using an alcohol-based solvent should provide measurably improved crush resistance—e.g., measurably slower release, when compared to similarly stressed particles with a coating produced from a high water content solvent.

In one embodiment, the use of the CR coating of the present invention will provide not more than about a 25% increase in API release measured at 5 minutes in a USP dissolution test as identified herein compared to an unstressed particle or dosage form. In another embodiment, the use of the CR coating of the present invention and the preferred granulates described herein will provide not more than about a 25% increase in API release measured at 5 minutes in a USP dissolution test as identified herein compared to an unstressed particle or dosage form.

The CR coating in accordance with the present invention comprises any polymeric material which would be acceptable for use in a pharmaceutical industry and whose solubility can be characterized as the following: the successful polymeric material will be at least sparingly soluble in an alcohol based solvent (a solvent containing at least about 90% alcohol by volume). Preferably, however, it is freely soluble in an alcohol based solvent. In contrast, the successful material will generally be no more than sparingly soluble in water. Often it is virtually insoluble in water. A sparingly soluble polymer is a polymer that requires 30 to 100 parts of a solvent to dissolve one part of the polymer. A freely soluble polymer requires only from about 1 to about 10 parts of the solvent to dissolve one part of the polymer. Note, however, that these are general requirements. If the manufacturer's literature of a particular material indicates that it is, for example, at least sparingly soluble in alcohol based solutions, then it can be a candidate for use in a CR coating, even if when measured by certain tests, its solubility would not fall into the ranges discussed above. Particularly preferred materials in accordance with the present invention are cellulose polymer materials applied with the aforementioned alcohol-based solvent. Other materials include include, but are not limited to ethylcellulose, methacrylate ester copolymers including Eudragit, RS, RL, E, NE, methacrylic acid copolymers including Eudragit L, S and Shellac.

In a particularly preferred embodiment, the polymer material is ethylcellulose. Ethylcellulose is an inert, hydrophobic polymer and is essentially tasteless, odorless, colorless, non-caloric, and physiologically inert. There are many types of ethylcellulose which can be used, as long as they meet the other requirements, such as alcohol solubility, discussed herein.

The ethylcellulose used can have different ethoxy content such as 48.0-49.5% described as N-type; 49.6-51.5% described as T-type; 50.5-52.5% described as X-type; all available from Aqualon, Hercules Research center, Wilmington, Del.

The ethylcellulose used can have different molecular weights such as including EC polymers of the N-type that form 5% w/w solution in toluene:ethanol (80:20) that have viscosity ranges of 5.6-8.0 cps described as N7; 8.0-11 cps described as N10; 12-16 cps described as N14; 18-24 cps described as N22; 40-52 cps described as N50; 80-105 cps described as N100.

Finally, the ethylcellulose can include different degrees of substitution of ethoxy groups per anhydroglucose unit, such as 2.65-2.81 for the X-type. N-type has values of 2.46-2.58.

The cellulose derivatives when dissolved or dispersed in an alcohol-based solvent as described herein may impart surprising properties, including added crush resistance in comparison to an identical coating applied with water alone, or a high water content solvent with less than about 90% alcohol by volume. Generally, the polymer to solvent ratio in a crush resistant coating before it is applied is about 1:100 to 1:10, and more preferably about 1:20 to 1:5, and most preferably about 1:15 to 1:7. Some amount of solvent may be detected in the resulting dosage form once the coating is dried. However it is preferred that the dosage form contains little if any residual solvent. These materials described for use in CR coatings may be used as a granulation binder, when used alone or with water soluble polymers as described herein.

The CR coating may also, optionally, include one or more of the following: 1) channeling agents; 2) plasticizers; 3) antitacking agents); 4) antifoaming agents; 5) colorant; and 6) viscosity modifiers.

Channeling agents, also called pore formers, can be added into the coating by being either dissolved or dispersed in the solvent and preferably are inert and will not chemically alter the polymer used in the coating. They are intended to leach out from the coat upon exposure to aqueous media (stomach content/intestine) creating channels within the coat to facilitate the drug release process. This term and mechanism are well recognized, but may not reflect an accurate description of what is taking place. Nonetheless, these materials are known as channeling agents. When properly used, by whatever name or mechanism, they can alter API release.

Examples of channeling agents include salts like sodium chloride, sodium carbonates, bicarbonate, citrate, calcium phosphates, potassium chlorides etc, sugars like sucrose, glucose, lactose, mannitol, sorbitol, polymers like HPMC, MC, HPC, CMC, polyethylene glycol, poloxamer, PVP, polyacrylic acid, polyvinyl alcohol and graft or block copolymers of such polymers, and preferably poloxamers. These can be included at levels of 0-50% based on of the dry polymer weight of the coating material, more preferred 1-40% and most preferred 5-30%.

Antitacking agents, also called antiadherent or glidants or separating agents, are used to reduce tackiness and agglomeration during the coating process and may be used herein. Examples of these materials include: magnesium stearate, calcium stearate, stearic acid, talc, kaolin, and stearyltrimethyl ammonium chloride. When used, they may be used at levels of 0-100% based on the dry polymer weight of the coating materials, more preferred 20-80%, most preferred 20-50%. Preferred is magnesium stearate.

Plasticizers may also be used in the coating to lower the glass transition temperature of the polymer to improve the film formation process during coating or subsequent heat treatment. They also impart flexibility. They are added to the coating by being either dissolved or dispersed in the solvent. Examples of plasticizers include triethyl citrate, triacetin, polyethylene glycols, propylene glycol, acetyl triethyl citrate, acetyl tributyl citrate, dibutyl phthalate, diethyl phthalate, tributyl citrate, dibutyl sebacate, diethyl sebacate, castor oil, Myvacet 9-40, Glyceryl tributyrate. These may be used at levels of 0-150% based on the dry polymer weight of the coating, more preferred 1-50%, most preferred 5-30%

Antifoaming agents in the coat may be used to reduce foam formation during coating solution/dispersion preparation process. Examples include silicon based antifoaming agent like Antifoam FG-10 made by Dow Corning. Antifoaming agents may be used at levels of 0-10% based on the polymer dry weight of the coating, 0.1-5% and 0.5-5%.

For product differentiation and aesthetic purposes, colorants may be used. Examples include FD&C and D&C lakes, titanium dioxide, magnesium carbonate, talc, pyrogenic silica, iron oxides, channel black, natural colorants and insoluble dyes. Colorants which may be used in an amount of 0-25% of the polymer dry weight of the coating, 0.5-10, 1-5%.

To reduce the polymer solution/dispersion viscosity while maintaining high polymer content to facilitate the coating process, viscosity modifiers may be used. Their level must be carefully selected to reduce the viscosity without any detrimental phase separation. Examples of these materials include salts with high order in the hofmeister's series including sodium citrate and sodium chloride which may be used at levels of 0-0.1 mol/liter of the coating solution/dispersion, more preferred 0.001-0.05, most preferred 0.005-0.03 mol/L, based on the weight of the coating.

Coatings, including the CR coatings of the invention may be applied by any known process, including but not limited to, spraying, dipping, pouring, spray drying, etc. It is also contemplated that the CR coating may be a single layer or multiple layers, having varying, or uniform crush-resistance layers. Generally, it is preferred that the CR coating has a thickness resulting in an average weight gain of a particle of about 30% to about 300%, and more preferably about 50% to about 200%, and most preferably about 65% to about 150%. These numbers reflect any coating additives as part of the coating. These average weight gain values correspond to the coating material being present in an amount of between about 20 and about 75% by weight of coated particle or granulate, and more preferably 40 to 60% by weight of the coated particle or granulate.

Before coating, the API containing particle may be in any form, including, but not limited to powders, crystals, granules, granulates, microgranules, beads, etc. These pre-coated API containing particles in accordance with the present invention preferably have an average particle size of about 100 to about 600 microns, and more preferably about 150 to about 500 microns, and most preferably about 200 to about 400 microns when tested by a sieve-shaking method. In another preferred embodiment, the pre-coated API containing particles preferably have a particle size distribution wherein no more than about 10% are less than 50 microns, and no more than 10% are larger than 700 microns. Of course, overs and unders could be discarded.

The CR coating may be applied as the outer most or inner most layer and non-CR coatings may be coated over, under or between CR coatings. It is also contemplated that the CR coating may be applied by any standard coating technique, including spraying, dipping, etc. The CR coatings of the present invention can also be used with other crush resistant and/or abuse-resistant strategies.

Once coated with the CR coating, it is generally preferred that the coated API containing particles have an average particle size of about 300 to about 1200 microns, and more preferably about 400 to about 1000 microns, and most preferably about 500 to about 800 microns when tested by a sieve-shaking method. In another preferred embodiment, the coated API containing particles preferably have a particle size distribution wherein no more than about 10% are less than 75 microns, and no more than 10% are larger than 1400 microns. Again, overs and unders could be discarded.

In another preferred embodiment of the present invention, used alone or in combination with other structures or elements, the CR coating, discussed above, also provides a controlled release of the API. The ethylcellulose of the CR coating, for example, may act as a controlled release material, enveloping the API within the coating and maintaining the desired release of the API. Other controlled release materials that may also be useful in accordance with the present invention may include but are not limited to hydroxypropylmethylcellulose (HPMC), hydroxypropyl cellulose (HPC), methylcellulose (MC), Hydroxyethylcellulose (HEC), carboxymethylcellulose (CMC), Methacrylate ester copolymers including Eudragit NE 30D, RS 100, RL 100, polyvinyl Acetate (PVA), Polyethylene oxide (PEO), shellac, zein, polylactic and polyglycolic acids polymers and copolymers, alginates, alginic acid, carbomers, fats, waxes, glycerol mono-, di-, tri-glycerides, Compritol, Precirol, gelucires, modified chitosans, carrageenans, and silicon elastomers.

Note that the above need not be limited to materials which can be applied from an alcohol base solvent or solution as described herein with regard to the crush resistant materials. However, same may be applied from that solvent system and may provide both crush resistance and controlled release. These materials may be applied in a single layer or multiple layers and may be applied using alternate materials or mixtures of materials. Thus, for example, a layer of HPMC may be used to coat the API material followed by a coating layer of, for example, ethylcellulose. These may be applied from the same or from different solvent systems and may include the same or different additives.

Generally, it is preferred that the controlled release material is ethylcellulose, meaning that it must be used in an amount that is capable of providing controlled release and crush resistance and should be applied from an alcohol based solvent. If used as both a CR coating and a controlled release coating, the amount of ethylcellulose needs to consider both functions. For controlled release, generally the amount of control release polymer coating material used in a coating is about 20 to 50, and more preferably about 10 to 60, and most preferably about 25 to 40. In addition, the API-containing particle may itself provide some measure of controlled release. For example, a wet granulate can be made from HPMC and ethylcellulose formulated using a water and alcohol solvent system. This material may itself provide some measure of crush resistance and/or controlled release.

Also considered useful in accordance with the present invention could be Clemente et al., U.S. Pat. No. 6,126,967, which issued on Oct. 3, 2000 relating to extended release of acetaminophen particles. Preferably the controlled release particles comprise a sugar/starch seed particle or solid support coated with a plurality of layers of acetaminophen and magnesium stearate that are bound with povidone. Most preferably the acetaminophen containing layers are coated with a plurality of layers of a mixture of povidone and magnesium stearate where the weight ratio of the acetaminophen to magnesium stearate ranges from about 5:1 to about 10:1 and the acetaminophen comprises about 70 to 80 percent of the controlled release particles. These are coated with the CR coating of the invention.

The CR coating of the present invention can be applied to any API-containing particle. These particles can be particles of the API alone, the API coated onto a sphere or nonpareil, a mixture of drug particles, or wet or dry granulated particles. In a preferred embodiment, the API-containing particle is a particle of the present invention including, without limitation, a wet granulate that aids in providing crush resistance to the coated particle. A wet granulate is a particle or agglomerate formed by wet granulation, which is a process by which particles, often smaller particles, are bound together in a granulator. Often a binder is used for this process, although some particles may be granulated in the presence of a solvent without a binder. In this instance, the additional amount of crush resistance can be measured as previously discussed with regard to the coating wherein the coatings are identical but the nature of the granulate is altered.

The wet granulate can be formed using any kind of solvent and/or binder. However, preferably, the binder is ethylcellulose provided in a solvent system of water and alcohol, wherein the amount of water ranges from about 5 to about 50 percent by volume, more preferably from about 10 to about 40 percent by volume, and most preferably between about 20 to about 30 percent by volume of the solvent. Additional excipients as traditionally used in granulates may also be used.

In another embodiment, the present invention relates to a granulate which provides adequate plasticity. This may be, but need not be, overcoated with the CR coating of the invention. These granulates may be wet or dry granulates which generally contain a relatively high percentage of selected polymers which are believed to provide, without meaning to be limited to any theory of operation, resilience, elasticity, plasticity and the like, resulting in something analogous to shock absorbency. While there may be some malleability and/or even deformation after a compressive force is applied, these materials may help dissipate the force and spread it across the entirety of the particle helping to prevent compromise of the CR coating. They may also provide excellent adherence with the coating, such that even if the coating were to crack, it is unlikely that significant chunks of the coating will flake off of the surface, thereby leaving large exposed gaps into which solvent may enter. In particularly preferred embodiments, certain modified celluloses such as hydroxypropymethylcellulose (HPMC), hydroxypropylcellulose (HPC) hydroxymethylcellulose (HMC), methylcellulose (MC), hydroxyethylcellulose (HEC), carboxymethylcellulose (CMC), and the like can be granulated with the API to provide a granulate with such plasticity. In one preferred embodiment, these modified celluloses are generally water soluble and generally insoluble in short chain normal alcohols such as $C_1$-$C_6$ alcohols. Without wishing to be bound by any particular theory of operation, it is believed that the elastic, plastic or shock absorbent properties that such high plasticity granulates can provide, particularly when used in combination with a CR coating in accordance with the present invention, provide additional crush resistance benefits.

Indeed, it has been observed that where two particles of similar size and identical API are coated with the same CR coating of the present invention, the high plasticity granulates of the present invention can provide a greater improvement in crush resistance than the same coated formulation with a different granulate.

In still another aspect of this embodiment, the granulate includes not only a polymer providing plasticity as described above, which is generally water soluble, but also a first material, preferably also providing plasticity, which is at least sparingly soluble, preferably, soluble in short chain normal alcohols and generally at most sparingly soluble in water. One such combination is a binder composed of HPMC and ethylcellulose.

The ethylcellulose is as previously described in connection with the CR coating. When HPMC is used in the granulate as the second slightly soluble material, the HPMC used can have different methyl to hydroxypropyl substitution percent ratios ranging from 30:0 in the A-type, 29:8.5 for the E-type, 28:5 in the F-type, 22:8 for the K-type all available from DOW Chemical Company, Midland, Mich. or any other HPMC polymers available from other suppliers such as Aqualon.

The HPMC used can have different molecular weights such as including HPMC polymers that form 2% w/w aqueous solution at 20° C. that have viscosity ranges of 15-4000 mPa·s for the A-type, 3-10,000 for the E-type, 50-4000 for the F-type and 3-100,000 for the K-type.

The present invention also, in a preferred embodiment, can provide for additional abuse resistance against the use of solvents. Readily available solvents which can be utilized to dissolve dosage forms safely are few. Water is certainly one. Ethanol, while dangerous, is a second. Other solvents may be available, but they are often inconvenient to obtain and/or can have debilitating, permanent side effects, which even an addict cannot ignore. For example, methanol or wood alcohol, is easy to find. However, it can cause blindness. This embodiment of the present invention utilizes two materials which, when exposed to a limited volume of alcohol, water, or a mixture thereof, forms a noninjectable mass ranging from an insoluble mass, to a gel, to a viscous slurry. It might also retard dissolution in these solvents.

By "limited volume" it will be appreciated that a small amount of a material that is, for example, at most slightly soluble in water (but at least soluble in, for example, ethanol, such as ethylcellulose), could nonetheless be dissolved, dispersed or at least diluted sufficiently that it could not form a noninjectable mass, given enough solvent. Thus, for example, while a tablet in accordance with the present invention could, once dissolved, form insoluble mass, a gel, or otherwise raise the viscosity of 20 mL of water sufficiently to retard injection, it would do little to change the properties of, for example, one liter of water or more. Of course, it would be difficult in such circumstances to inject that liter into the body to obtain the desired "high." Generally, a limited volume in accordance with the present invention is defined as 50 milliliters or less, more preferably 20 milliliters or less and even more preferably 10 milliliters or less and most preferably 5 milliliters or less (volumes which could be injected). Thus, the first slightly soluble material used in the dosage form must be of a type and available in an amount which is sufficient to allow it to form a noninjectable mass and the second slightly soluble material must be capable of doing the same when the dosage form containing both is dissolved (which includes partially dissolved or where an attempt is made to make it dissolve) in a limited volume of water, alcohol or both.

Any material which can meet the foregoing qualifications may be used in accordance with the present invention. Successful materials are polymeric, generally not crystalline, not highly crosslinked, preferably have some degree of solubility in water or alcohol and are pharmaceutically acceptable. Preferred, however, are cellulose materials including ethylcellulose, HPMC, MC, HPC, and the like. These granulates may be produced using binders and solvent system as appropriate for wet granulation thereof. In a particularly preferred embodiment, the wet granulate includes both ethylcellulose (EC) and hydroxypropylmethylcellulose (HPMC) granulated in a solvent system comprising both water and ethanol. Thus, the wet granulate described previously as well as the crush resistant granulate providing plasticity can also provide solvent resistance and/or retard injectability. Preferably the amount of plasticizing polymers in the granulate will range from about 20 to about 90 percent by weight, more preferably between about 30 to about 90 percent by weight, and most preferably between about 35 to about 90 by weight of the granulate when the granulate includes both EC and HPMC, the HPMC will generally range from about 15 to about 80 percent by weight, more preferably between about 20 to about 70 percent by weight, and most preferably between about 30 to about 50 by weight of the uncoated granulate. The balance of this granulate will be API and any excipients conventionally used in granulation techniques. These may be coated with one or more coatings including the CR coatings of the invention.

More specifically, a wet granulate in accordance with this aspect of this embodiment of the present invention includes at least three ingredients. The first is a first material that is at most slightly soluble in water but is at least soluble in alcohol. Generally this first slightly soluble material is selected from natural and synthetic starches, natural and synthetic celluloses, acrylics, vinylics and resins. More preferably, the first material is selected from ethylcellulose, Eudragit RS, RL, E, NE, L, S, and shellac. Most preferably, the first gelable material is ethylcellulose.

The amount of first slightly soluble material present in the granulate will depend on a number of factors; including without limitation, the API used, the dose of API to be administered as part of each dosage form, the size of the dosage form, the desired viscosity or gelling desired upon exposure to the correct solvent, and the nature of the first material. However, generally, the amount of first material that is at most slightly soluble in a limited volume of water in the granulate will range from between about 1 to about 90% by weight of the uncoated granulate, more preferably from between about 5 to about 75% by weight of the granulate, and most preferably about 10 to about 40%.

The second material found within the granulate is a second slightly soluble material. This material is at most slightly soluble in alcohol but is at least freely soluble in the same volume of water. Like the first slightly soluble material, any material that is safe for ingestion or injection and can form a noninjectable mass under the specified condition is contemplated. However, preferably the second slightly soluble materials are selected from the same general categories as the first slightly soluble material; namely, natural and synthetic starches, natural and synthetic celluloses, acrylates, and polyalkylene oxides. Natural and synthetic celluloses are preferred for both the first and second slightly soluble materials. In a particularly preferred embodiment, the second gelable material is selected from hydroxypropylmethylcellulose, methylcellulose, hydroxyethylmethylcellulose, sodium carboxy methylcellulose, hydroxyethylcellulose or polyethylene oxide. The amount of the second slightly soluble material present in the granulate will depend on the same criteria as previously described in connection with the first gelable material. However, generally, the amount will range from between about 1 to about 90% by weight of the uncoated granulate, more preferably between about 10 to about 75% by weight of the granulate, and most preferably between about 20 to about 50% by weight of the granulate.

When ethylcellulose is used in this embodiment (or indeed in any embodiment herein), it can have different ethoxy content such as 48.0-49.5% described as N-type; 49.6-51.5% described as T-type; 50.5-52.5% described as X-type; all available from Agualon, Hercules Research center, Wilmington, Del.

The ethylcellulose used can have different molecular weights such as including EC polymers of the N-type that form 5% w/w solution in toluene:ethanol (80:20) that have viscosity ranges of 5.6-8.0 cps described as N7; 8.0-11 cps described as N10; 12-16 cps described as N14; 18-24 cps described as N22; 40-52 cps described as N50; 80-105 cps described as N100.

Finally, the ethylcellulose can include different degrees of substitution of ethoxy groups per anhydroglucose unit, such as 2.65-2.81 for the X-type. N-type has values of 2.46-2.58.

There are no specific particle size limitations with regard to the first or second slightly soluble materials in accordance with the present invention. However, the materials should be sufficiently small so as to enhance their ability to rapidly form a noninjectable mass.

As described above, the granulate comprises a first slightly soluble material and a second slightly soluble material. However, the granulate may include more than one material that is at most slightly soluble in water and is at least soluble in alcohol and/or more than one second material that is at most slightly soluble in alcohol but is at least soluble in water. In addition, a third or more slightly soluble material(s) may be added to provide a similar level of solvent abuse resistance as needed.

Wet granulation is typically accomplished using a solvent or diluent. Any solvent which is conventional for use in producing granulates are contemplated herein. Preferred solvents in accordance with the present invention include water, short chain alcohols ($C_{10}$ or less) which may be normal, branched, denatured, and the like, low molecular weight ketones such as acetone and methyl ethyl ketone and the like. In a particularly preferred embodiment, the solvent system used to produce the granulate is a mixture of alcohol, and more preferably ethanol, and water. It has been found that when this material is used in granulation, particularly when used in connection with ethylcellulose, it can provide enhanced crush resistance and/or controlled release. The solvent mixture in this instance comprises between about 10 and about 30% water with the balance being alcohol, and more preferably between about 20 and about 30% water with the balance being alcohol. The ethylcellulose may be part of the granulate as a cogranulate to which a solvent and/or binder is added or may be dissolved, dispersed, suspended, or mixed with the solvent and added to the granulate as a part of the binder.

In general, the binder may be formed in situ (adding a solvent to a dry material that, when wetted, serves as a binder) or may be sprayed on or mixed with a solvent. In some instances, the solvent itself may serve as a binder. Moreover, one or more of the ingredients to be contained within the granulate can be introduced as part of the binder and/or as part of a solvent system. Thus, for example, the API could be dissolved, dispersed, suspended, or mixed with the solvent and/or with the binder and applied to the surface of the particulate of the first and/or second slightly soluble materials or some other component of the granulate. This is also true for the excipients described previously.

The granulate in accordance with the preferred embodiment of the present invention, however, also needs to provide certain protections against abuse by drug users through injection. The presence of the first and second slightly soluble materials is meant to ensure that if the dosage form or its contents are attempted to be dissolved in water, alcohol, or a mixture thereof, the result will be a noninjectable mass which is a viscous, insoluble and/or gel-like material. One might think that the amount of first and second slightly soluble materials would be the same in the granulate. Although that is a possibility, it is not necessarily the case. Factors such as molecular weight, solubility and the like can mean that significantly more of one material is needed to obtain the same relative effect than the other. In terms of the dosage form, however, what is important is that there is a sufficient amount of each material to ensure that if the dosage form is dissolved (or an attempt to do so is made) in a relatively small volume of water, alcohol or a mixture, an amount which is consistent with a drug abuser's intent to inject or even snort the resulting liquid, attempting to dissolve the dosage form in either water or, the resulting noninjectable mass will make it very difficult and unattractive to the user.

Thus, the amount that is necessary of the first slightly soluble material and the second slightly soluble material is preferably an amount which is sufficient to ensure that upon exposure to 20 milliliters of water and/or ethanol as appropriate, a noninjectable mass as described above will be formed rendering abuse less likely. More preferably, the amount must be sufficient to ensure the formation of the noninjectable mass upon exposure to 10 milliliters of water or ethanol as appropriate. Generally, however, the amount of first slightly soluble material present in the dosage form ranges from between about 0.1 to about 50% by weight, or preferably between about 1 to about 20% by weight. The amount of the second slightly soluble material generally ranges from between about 0.1 to about 50% by weight and more preferably between about 1 to about 30% by weight. These are based on the weight of the dosage form not on the weight of the granulate. Thus, in general, the amount of granulate generally found within each dosage form ranges from between about 0.1 to about 90%, more preferably from between about 10 to about 75%, and most preferably between about 20 to about 50% by weight. As above, and elsewhere herein, the weight percentages are as to a dosage form or as to the total composition prior to creating a dosage form.

Excipients which may be used in accordance with the present invention to form granulates include those which are traditionally used in oral dosage forms. In a preferred embodiment, the granulate may include any excipients as desired, which are then measured into a granulator.

More particularly, in one aspect, the present invention relates to a method of increasing the abuse resistance of a dosage form comprising the steps of forming a wet granulate as previously described from a first gelable material, a second gelable material, both as defined herein, and an active pharmaceutical ingredient. Preferably, this granulation is accomplished using a solvent of water and ethanol. Preferably, the granulate is then dried to a target moisture content level. It is not necessary that the material be dried or that the material be dried in an oven tray or other device. It may be left to air dry. The granulate can be coated before or after drying (or when a coating is applied in a fluidized bed, the processes can go on nearly simultaneously) and then mixed with at least one excipient as described herein and preferably compressed into tablets as just described. There can be more than one coating and any coatings used can include a CR coating as described elsewhere herein.

In a further preferred embodiment, the present invention provides a pre-dosage form composition that may provide a chemical barrier to a pharmaceutically active ingredient in a resultant dosage form. The composition comprises a combination of at least two differing particles—a first particle that comprises the pharmaceutically active ingredient which can include, without limitation, a CR coated particle, a solvent/crush resistant granulate, such as one made with ethylcellulose and HPMC, and such granulates coated with a CR coating as described herein are contemplated for this first particle. The composition also includes a second particle comprising a fat/wax material—the combination of which is used to prepare a resultant dosage form. By virtue of the mixture and combination of the particle system of the invention, the dosage form may exhibit resistance to chemical tampering—specifically solvent-accelerated active ingredient release. Thus, the invention may help to retain the release rate consistent with the initial desired rate of active ingredient release, thereby frustrating dose dumping attempts associated with abuse. To provide even further tamper-resistant properties, this preferred embodiment can be used in conjunction with other abuse-resistance technologies, such as crush-resistant particles, crush-resistant coatings, and/or barrier bead technology.

A dosage form prepared using this composition may afford two chemical barriers that resist chemical degradation—namely solvent-accelerated release of the active ingredient. According to this embodiment, the first particle containing the active ingredient can itself further comprise a coating material on the first particle, can be granulated to provide crush and/or solvent resistance or may be both granulated and coated as described. The second barrier may result from the combination of the second fat/wax particle in proximity to the first active particle, wherein it is believed, without limitation, that two particles in combination form a matrix limiting the extent of solvent access to the active particles.

Particle sizes can vary between first and second particles or among the individual particles within the same particle type. Also, different active particles and active particles with differing excipients/secondary ingredients, can be combined within a given single composition of the invention.

The first particle containing the active ingredient can be in the form of powders, granules, crystals, agglomerates, microcrystals, microgranules, microcapsules, and the like alone or with one or more excipients. Preferably, the first particle is in the form of a granule. The first particle can contain, in addition to the active pharmaceutical ingredient, secondary ingredients and excipients within the first particle composition.

Preferably, the first particle containing the active ingredient is coated. With regard to a coated particle embodiment, the first particle can be coated with a coating material that provides additional crush resistance and/or controlled release of the pharmaceutically active ingredient contained in the particle composition. Controlled release can be delayed release, such as enteric coating or extended release coating that slows the delivery of the drug over time, generally between one to twenty-four hours for example.

In general, fat/wax materials suitable for use in the second particle can include any fatty (lipid) or waxy material derived from natural origin, including animals and plants, or those obtained through semi-synthetic or synthetic processes. These can include structurally unmodified or chemically modified materials (e.g., phospholipids), provided they are non-toxic to humans. More specifically, fat/wax materials that can be used in the second particle include, but are not limited to, fatty acids (saturated, trans, monounsaturated, polyunsaturated) esters of glycerol, propylene glycol, polyethylene glycols, polyoxyethylene (mono- or di-esters), and the like. Combinations of fat/wax materials can also be used. The fat/wax material can be selected according to the melting point as well, i.e., low (e.g., lower than body temperature), medium or high (above 60° C.) melting point lipids and waxes. Thixotropic fats/waxes can also be used.

Suitable fat/wax ingredients for the second particle include glycerol fatty esters, fatty glyceride derivatives, waxes and fatty alcohols such as, for example, COMPRITOL® (glycerol behenate), PRECIROL® (glycerol palmitostearate), GELUCIRE® (stearoyl macroglycerides), carnauba wax, bees wax, microcrystalline wax, cetyl alcohol.

According to the invention, the second particle containing the fat/wax material is present in the pre-dosage form composition in an amount sufficient to resist solvent-accelerated release of the pharmaceutically active ingredient from the first particle.

The second particle containing the fat/wax material can contain from about 1% to about 50% fat/wax particles per dosage form unit (e.g., tablet). Preferably, the dosage form unit can contain from about 2.5% to about 30% fat/wax per unit, most preferably from about 5% to about 25%, per total dosage form unit. These weight percentages are also for the weight percentage in the pre-dosage form composition, which would contain weight percentages equal to the final dosage form.

In one solvent acceleration active release scenario, dosage forms prepared with the pre-dosage form of the invention may be co-ingested with alcohol—either intentionally or accidentally. Under these circumstances, the chemical barrier associated with the composition may afford maintained resistance to alcohol within the gastric environment for a period sufficient to resist substantial degradation of the protective barrier effects of the fat/wax particles.

It may be possible to modify the active-to-fat/wax ratio to provide the optimal effect with regard to the potential chemical solvent resistance properties of the dosage form. Balancing chemical or solvent resistance versus desired delayed release parameters of the dosage form should also be considered. Accordingly, two general factors may be involved: first, the thickness and type of coating material employed; and second, the amount of fat/wax particles in the dosage form. In other words, release of active ingredient could be controlled by modifying the coating/extended release material in combination with the dual particle system which might create a tortuous path that delays the chemical or solvent access to the first active particle hence drug diffusion. Variations in these factors affect the chemical resistance and delayed release parameters, in addition to physical tampering/crush resistance.

The first particle containing the active ingredient and the second particle containing the fat/wax material can be combined to form mixture of granular or particulate prior to forming the resulting dosage form. The first particle may be the wet granulates described herein and/or may be coated with a CR coating of the invention. At this juncture, for example, additional or secondary ingredients can be combined with the pre-dosage form composition as part of the process of preparing the resultant dosage form, e.g., tablet. For example, the dosage form formulation can include spray-dried lactose and EMCOMPRESS (dibasic calcium phosphate dehydrate).

In another embodiment, the composition of the invention can be further combined with a crush resistant component. The resultant dosage form would be a collective tamper-resistant dosage form, thus providing protection against both chemical tampering and physical tampering to prematurely release the active ingredient from the dosage form.

In a further alternate embodiment, the present invention may contain crush resistance particles in the form of barrier beads. A barrier bead is any structure which may be ingested, is compatible with a dosage form formulation and is able to impart some measure of crush resistance to a mixture or dosage form by protecting the substructure and/or function of any API containing particles contained therein. Often, a barrier bead in accordance with the present invention is made from a material that is more resilient to compression than the particles they are meant to protect.

In one embodiment, these barrier beads can be made from sugar spheres or carrier particle traditionally used in the pharmaceutical industry for drug delivery. In general, the barrier beads of the present invention are not coated with an API containing layer. However, the barrier beads of the present invention may themselves be coated and can even be coated with multiple layers, one of which being an API containing layer. They could also be, for example, a rigid matrix particle having an API adsorbed thereon. However, they must be sized and present in an amount which is sufficient to reduce the crushing of other API containing particles within the mixture or dosage form. And, as they will take the brunt of any compressive force applied, the coatings used and the release of the API from any coated barrier beads must be expected to be compromised. Thus, for example, a first API could be coated on a carrier particle and coated with a controlled release coating. These could be mixed with, for example, a second API coated particle which employed a carrier particle that had an average particle size that was larger than the average particle size of the first API coated particle and was more resilient to crushing. The first particle would be an API containing particle in accordance with the invention and the second would be a barrier bead. When the mixture was crushed, the coating on the barrier bead could be compromised and would likely be compromised to a greater degree than the controlled release coating on the first particle—the API containing particle. This is, however, just a non-limiting illustration. Indeed, in a preferred embodiment, the barrier bead has no coating, no API or neither of them.

In a preferred embodiment, in accordance with the present invention, the barrier bead can be composed of, for example and without limitation, particles, crystals, granulates, capsules, mini-tablets microparticles, microgranules, microcrystals or microcapsules, carrier particles, spheres or nonperells. Particles, granules and crystals have their traditional meaning. "Capsule" when used in connection with a particle (not dosage form) in accordance with the present invention includes generally hollow, spherical vessels such as liposomes, micelles and the like. These may be dried. "Micro" in the context of barrier beads means a particle having a particle size of below about 50 microns. Preferably the barrier beads are substantially spherical although dimensions can vary and shapes used can be, without limitation, elliptical, generally egg-shaped, rod-shaped, regular and/or irregularly shaped. They may also be in the shape of polygons and cylinders, pyramids, rods, cones, hexagons, discs, cubes, rectangles or any combination of any of the forgoing. Indeed, there may be an advantage to having non-spherical barrier beads as that can limit their movement and their ability to role and crush smaller API containing particles.

Barrier beads can be composed of any number of materials or mixtures thereof including particles created from one or more of the taste masking materials, polymers, fats, lipids, carbohydrates, waxes, salts or minerals. The barrier beads comprised of a single or a mixture of materials can be manufactured through pan coating, fluid bed coating, granulation process including high shear granulation, top spray fluid bed granulation, spray-drying, spray-congealing, spray-chilling and lyophilization with or without subsequent milling to achieve target particle size distribution. Other barrier bead manufacturing methods beyond the aforementioned examples are also contemplated.

However, in a preferred embodiment, the barrier beads are made of a sugar. "Sugar" in accordance with the present invention generally includes other forms of carbohydrate such as, for example, sugars, sugar alcohols, ketoses, saccharides, polysaccharides, oligosaccharides and the like, as well as celluloses and modified celluloses. These include, without limitation, sucrose, mannitol (spray dried and granular) lactose, and microcrystalline cellulose. Most preferred in accordance with the present invention are sucrose and microcrystalline cellulose. Useful sucrose spheres are available from Paulaur Corp., 105 Melrich Road, Cranbury, N.J. 08512. Useful microcrystalline spheres are sold by Asahi Kasei Chemicals Corp, with the following address: Hibiya-Mitsui Building 1-2 Yurakucho 1-chome, Chiyoda-ku, Tokyo 100-8440 Japan under the designation CELPHERES.

The size of the barrier beads can vary considerably with, amongst other things, the application, the size, shape and structure of the API containing particle, volume of the barrier beads that will be used in the formulation, the type of dosage form in which they will be included, their shape and the material used to form the barrier beads. Particularly important is the relative size of the API containing particles. It is possible to use barrier beads that are smaller than the API containing particles, e.g., the average particle size of the barrier beads is 25% less by weight, measured by sieving, than the average particle size of the API containing particles. However, it is generally preferred that the average particle size of the barrier beads be about equal to or larger than the average particle size of the API containing particles, again measured by weight based on sieving. More preferably, the barrier beads range in average particle size of from about 1 to about 5 times the average particle size of the API containing particles, more preferably about 1 to about 3 times, and even more preferably about 1 to about 1.5 times the average particle size of the API containing particles.

In one preferred embodiment, not only are the barrier beads about the same size (about 1 to about 1.5 times the size) as the average particle size of the API containing particles, but they are also the same shape and color as the API containing particles. This makes it difficult for an abuser to distinguish the barrier beads from the API containing particles further frustrating any attempt to abuse that mixture or dosage form.

In accordance with the present invention, the barrier beads have a size that generally ranges from between about 180 microns and about 1800 microns, more preferably between about 300 microns and about 1200 microns and most preferably between about 500 and about 850 microns. This means that the average particle size of the barrier beads, when measured by sieving and based on weight, will fall within those ranges. In a preferred embodiment, however, the particle size of the barrier beads is very uniform in terms of distribution, often more uniform than the API containing particles. In one particular embodiment, the barrier beads are sized such that at least about 75% of the barrier beads, by weight, fall within these ranges based on sieving.

Generally in mixtures, and in dosage forms as well, of the present invention, the barrier beads constitute between about 10 and about 90 percent by weight, more preferably between about 30 and about 90 percent by weight of the mixture or dosage form, and most preferably between about 60 and about 90 percent by weight of the mixture or dosage form. The balance of the mixture or dosage form would be the API containing particles and any additional ingredients or excipients. The API containing particles can be present in an amount of between about 0.1 and about 90% by weight of the dosage form or mixture.

In one embodiment, the ratio of the barrier beads to the protected particles (e.g., controlled release particles, crush resistant particles, taste masked particles) is from about 10:90 to about 75:25, more preferably from about 75:25 to about 90:10.

In another embodiment, the ratio of barrier beads to API particles (including protected particles) is greater than 50:50 to about 90:10, more preferably about 55:45 to about 85:15 and even more preferably from about 60:40 to about 85:15 by weight. In still another embodiment, at least about 66% of the collective of barrier beads and API particles is composed of barrier beads.

In another embodiment, the majority of the combined weight percent of barrier beads and API particles are barrier beads having an average particle size, as measured by sieving, which is from up to 25% less than the average particle size of the API particles to up to 50% greater than same.

In another embodiment, the majority of the combined weight percent of barrier beads and API particles are barrier beads and the API particles also include at least one additional crush resistance feature or structure, such as a robust granulate or crush resistant coating.

Dosage forms of this aspect of the invention can be prepared according to the following process. To prepare the first particle of the composition of the invention, the pharmaceutically active ingredient can be mixed with polymers in a granulator first as a dry mix. Then, the polymer solution can be added to the mix, and the process continues while adding the solution until granulation is achieved. The resulting granules can be partially dried until the desired loss of drying value is reached for the given formulation. The granules can then be milled in a granular mill and then dried to a LOD of less than 5%, for example.

Next, the granules can then be coated (with ethylcellulose in ethanol solution, for example), with magnesium stearate, in a bottom spray fluid bed, until the desired coat level is obtained. The granules can then be mixed together with the second particle fat/wax (second particle) and other excipients.

While at least one API is required, it is contemplated that multiple APIs may also be used. "API", or Active Pharmaceutical Ingredient, in accordance with the present invention include materials capable of being particles, materials likely to be abused by people, or otherwise useful in the present invention. Such active ingredients may include systematically distributable pharmaceutical ingredients, vitamins, minerals, dietary supplements, as well as non-systemically distributable drugs. A combination or mixture of any of the foregoing is also contemplated by the present invention. Pharmaceutical ingredients may include, without limitation, antacids, analgesics, stimulants, sleep aids, hypnotics, antipyretics, antimicrobials, anxiolytics, laxatives, antidepressants, antidiuretics, antiflatuants, antispasmodics, antiinflammatory, antibiotics, diuretics, anorexics, antihistamines, antiasthmatics, antidiuretics, antiflatuents, antimigraine agents, antispasmodics, sedatives, antihyperactives, antihypertensives, tranquilizers, decongestants, immunosuppressants, anticancers, antivirals, antiparasitics, antifungals, antiemetics, antidepressants, antiepileptics, local anesthetics, vasoactive agents, antiasthmatics, skeletal muscle relaxants, drugs for parkinsonism, antipsychotics, hematopoietic growth factors, antihyperlipidemics, anticoagulants, fibrinolytics, antithrombotics, hormones, therapeutic proteins and peptides, antiarrhythmia, antiangina, beta blockers and combinations thereof. Also included as API's in accordance with the present invention are the drugs and pharmaceutically active ingredients described in Mantelle, U.S. Pat. No. 5,234,957, in columns 18 through 21. That text of Mantelle is hereby incorporated by reference. In one embodiment in accordance with the present invention, the APIs are preferably pharmaceutical agents having a high likelihood of abuse by people. In another preferred embodiment of the present invention, the API is a pain medication such as an a narcotic or non-narcotic analgesic as listed on pages THER-2 and THER-3 of The Merck Index, 13th Ed., Published by Merck & Co., Inc., of Whitehouse Station, N.J., copyright 2001, which is hereby incorporated by reference. The narcotic analgesics include, but are not limited to, analgesics, pain relievers, opioids such as oxycodone, codeine, hydrocodone, morphine, hydromorphone, oxymorphone, methadone, propoxyphene, meperidine, fentanyl, buprenorphine, butorphanol, dezocine, levomethadyl acetate, levorphanol, nalbuphine, pentazocine, remifentanil, sufentanil, tramadol; Stimulants like amphetamine, methamphetamine, dexamphetamine, methylphenidate, dexmethylphenidate, pemoline; Sedative and hypnotics including barbiturates as amobarbital, aprobarbital, butabarbital, mephobarbital, phenobarbital, secobarbital; benzodiazepines such as alprazolam, clonazepam, diazepam, estazolam, flurazepam, halazepam, lorazepam, midazolam, quazepam, temazepam, triazolam, prazepam, oxazepam, other drug classes include modafinil and armodafinil. A particularly preferred API is oxycodone.

As used in this disclosure, the term "vitamin" refers to trace organic substances that are required in the diet. For the purposes of the present invention, vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes that may be useful in the present invention include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP) Coenzyme A (CoA) pyridoxal phosphate, biocytin, tetrahydrofolic acid, coenzyme $B_{12}$, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

It is contemplated that the composition of the present invention may also include at least one other ingredient including, but not limited to, at least one other API, taste masking agents, fillers, cogranulates, disintegrates, binders, flavors, etc, which may be co-milled with the at least one API, separately milled, mixed, etc.

The amount of API in the composition can vary greatly and can depend upon, among other things, the type and properties of the API, the density, friability, hardness, etc. of the API, the condition it is intended to treat, the size of the particle, the size and nature of the dosage form it is intended to be used in, whether or not more than one API is to be delivered from the dosage form, whether or not the API containing particle is a granulate or includes one or more excipients and the like. In terms of the proportion of the uncoated particle that is API, that can range from about 0.1% to about 90% by weight of the uncoated particle or granulate, and more preferably in an amount of about 1% to about 60% by weight, and most preferably in an amount of about 10% to about 40% by weight of the uncoated particle. In terms of the proportion of the coated particle that is CR coating, that can range from about 20% to about 75% by weight of the coated particle, and more preferably in an amount of about 33% to about 67% by weight, and most preferably in an amount of about 40% to about 60% by weight of the coated particle.

As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA.

The amount of granulates and/or coated particles within a dosage form can vary greatly and can depend upon, among other things, the type and properties of the API, the density, friability, hardness, etc. of the API particles, the condition it is intended to treat, the amount and size of other ingredients, the size of the coated particle, the composition, content and amount of API in the coated particle, the size and nature of the dosage form, the number of dosage forms per dose, whether or not more than one API is to be delivered from the dosage form, etc. It is preferred that the dosage form provide a therapeutically effective amount of at least one API to a patient in need thereof. The coated particles are preferably present in one or more dosage forms in an amount sufficient to provide a therapeutically effective amount the at least one API. A "therapeutically effective amount" is the amount or quantity of an API or active ingredient which is sufficient to elicit the required or desired therapeutic response, or in other words, the amount which is sufficient to elicit an appreciable biological response when administered to a patient. The dosage need not be optimal, nor even provide a cure or symptomatic relief. Generally, the total amount of coated particles for any individual dosage form is an amount which is capable of providing between about 1 microgram and about 2 grams of API per dosage form, more preferably from about 0.1 milligram and about 1 gram of API per dosage form and even more preferably from about 1 milligram to about 800 milligrams per dosage form. Dosage forms can be in any size and shape, but preferably of a size and shape to avoid crushing or abuse.

It is contemplated that the crush resistant/solvent resistant dosage forms in accordance with the present invention, may be made from any one or any combination of the previously disclosed granulates and/or CR coated particles alone or may also include at least one other ingredient or excipient. The at least one other ingredient or excipient may include, but is not limited to, other APIs, taste masking agents, binders, fillers, sugars, artificial sweeteners, polymers, flavoring agents, coloring agents, lubricants, glidants, bio- or muco-adhesives, viscosity modifiers, surfactants, buffers, disintegrants etc. The amount of any one or more of these ingredients will vary with the amount of CR coating (including ethylcellulose), additional polymers, API, API particle size, and shape of the dosage form, form of the dosage form, how many ingredients are used, which ingredients are used, the number of dosage forms that will make-up a dose, the amount of API per dose and the like. Any combination or amounts are contemplated sufficient to allow the creation of a crush-resistant, solvent-resistant, storable dosage form in accordance with the present invention.

"Taste masking agent(s)" in accordance with the present invention include anything known to be used as a taste masking agents in this art. Preferred taste masking agents in accordance with the present invention may include Eudragit E-100, ethylcellulose, hydroxypropylmethylcellulose, hydroxypropyl cellulose, methylcellulose, Hydroxyethylcellulose, carboxymethylcellulose, shellac, zein, carbomers, fats, waxes, glycerol mono-, di-, tri-glycerides, Compritol, Precirol, gelucires, poloxamers, modified chitosans, carrageenans, cellulose acetate trimellitate, hydroxypropyl methylcellulose phthalate, hydroxypropylmethylcellulose acetate succinate, methacrylic acid copolymers including Eudragit L 100, S 100, L30D-55, polyvinylacetate phthalate (PVAP). Taste masking agents can be used in conventional amounts and preferably in an amount of about 0 to about 50% by weight of the total dosage form, and more preferably in an amount of about 5% to about 40% by weight of the total dosage form, and most preferably in an amount of about 10% to about 30% by weight of the total dosage form.

Binders can be anything known to be used as binders. These materials are used to add cohesiveness to powders and provide the necessary bonding to form granules that can be compressed into hard tablets that have acceptable mechanical strength to withstand subsequent processing or shipping and handling. Some binders that may be useful in the present invention include acacia, tragacanth, gelatin, starch (both modified or unmodified), cellulose materials such as methylcellulose, ethylcellulose, hydroxypropylmethylcellulose, hydroxypropyl cellulose, Hydroxyethylcellulose and sodium carboxy methylcellulose, alginic acids and salts thereof, magnesium aluminum silicate, polyethylene glycol, guar gum, polysaccharide acids, bentonites, sugars, invert sugars, and the like, fats, waxes, polyvinylpyrrolidone, polymethacrylate and other acrylic and vinyl-based polymers. Binders can be used in conventional amounts and preferably in an amount of about 0 by weight to about 50 and more preferably about 2 to about 10 percent by weight of the total dosage form.

Fillers can be anything known to be used as fillers. Some fillers that may be useful in the present invention include mannitol, dextrose, sorbitol, lactose, sucrose, and calcium carbonate. Fillers can be used in conventional amounts and preferably in an amount of about 0 to about 90, and more preferably about 10 to about 50.

A particularly preferred type of filler which may be used is sugars. Sugars that may be used in the present invention include sugar, sugar alcohols, ketoses, saccharides, polysaccharides, oligosaccharides and the like, as well as celluloses and modified celluloses.

Sugars may also include direct compression and/or nondirect compression sugars. Particularly preferred nondirect compression sugars include, without limitation, dextrose, mannitol, sorbitol, trehalose, lactose and sucrose. Of course, these sugars generally exist as either a direct compression sugar, i.e., a sugar which has been modified to increase its compressibility and/or flow, or a nondirect compression sugar which does not have sufficient flowability and/or compressibility to allow it to be used in high speed processing and multi-tablet presses without some sort of augmentation such as, without limitation, a glidant to increase flow, granulation to increase flow and/or compressibility and the like. Of course, techniques like granulation can also be used to convert something which initially has sufficient flow and compressibility to be considered a direct compression sugar before processing into a nondirect compression sugar as well. This can be measured by directly compressing tablets made only from a sugar and comparing the flow and compressibility both before and after processing. If flow and/or compressibility are reduced after processing the material is likely to have become a nondirect compression sugar. It will be appreciated however, that whether or not the reduction in properties are sufficient to require augmentation or further processing before the sugar is used in a commercial process will depend on a number of factors including the amount used, the type of processing equipment used, and the overall formulation. Generally, however, some further processing or augmentation is required. While not definitive, sometimes a nondirect compression sugar will have at least about 90% of its particles smaller than about 200 microns, and more preferably 80% smaller than about 150 microns.

The amount of total sugar can range from about 0 to about 90. More preferably, the amount of sugar will range from about 5 to about 75, and even more preferably between about 10 and 50. Other non-carbohydrate diluents and fillers which may be used in accordance with the present invention include for example dihydrated or anhydrous dibasic calcium phosphate, tricalcium phosphate, calcium carbonate, anhydrous or hydrated calcium sulphate, and calcium lactate trihydrate. When used these are present in an amount of ranging from 0 to about 90, more preferably from about 5 to about 75 and most preferably from about 10 to about 50% by weight of the dosage form.

Artificial sweeteners can be anything known to be used as artificial sweeteners. Some artificial sweeteners that may be useful in the present invention without limitation include saccharin, aspartame, sucralose, neotame, and acesulfame potassium. Artificial sweeteners may be used in conventional amounts, and preferably in an amount ranging from about 0.1 to about 2.

Flavoring agents can be anything known to be used as flavoring agents. Flavoring agents that may be useful in the present invention may include synthetic flavor oils and flavoring aromatics and/or natural oils, extracts from plants, leaves, flowers, fruits and so forth and combinations thereof. These may include cinnamon oil, oil of wintergreen, pepmint oils, clove oil, bay oil, anise oil, eucalyptus, thyme oil, cedar leave oil, oil of nutmeg, oil of sage, oil of bitter almonds and cassia oil. Also useful as flavoring agents are vanilla, citrus oil, including lemon, orange, banana, grape, lime and grapefruit, and fruit essences, including apple, pear, peach, strawberry, raspberry, cherry, plum, pineapple, apricot and so forth.

Flavoring agents may be used in conventional amounts, and preferably in an amount ranging from about 0.01% to about 3% by weight of the dosage form, and more preferably from about 0.1% to about 2.5% by weight of the dosage form, and most preferably from about 0.25% to about 2% by weight of the dosage form.

Coloring agents can be anything known to be used as a coloring agent. Coloring agents useful in the present invention may include titanium dioxide, and dyes suitable for food such as those known as F.D.& C. dyes and natural coloring agents such as grape skin extract, beet red powder, beta-carotene, annatto, carmine, turmeric, paprika, etc. Coloring agents may be used in conventional amounts, and preferably in an amount ranging from about 0.001% to about 1% by weight of the dosage form.

Lubricants can be anything known to be used as a lubricant. Lubricants that may be useful in the present invention may include intrinsic or extrinsic lubricants. Intrinsic lubricants may include magnesium, calcium, zinc salts of stearic acid, hydrogenated and partially hydrogenated vegetable oils, animal fats, polyethylene glycol, polyoxyethylene monostearate, talc, light mineral oils, sodium benzoate, sodium lauryl sulphate, magnesium oxide and the like. Lubricants may be used in conventional amounts, and preferably in an amount from about 0.1% to about 5% by weight of the dosage form, more preferably from about 0.25 to about 2.5 and most preferably from 0.5 to 2%.

Viscosity modifiers can be anything known to used as a viscosity modifier. Some viscosity modifiers that may be useful in the present invention include, without limitation, sodium alginate, hydroxypropyl methylcellulose (HPMC), hydroxyethylcellulose (HEC), sodium carboxymethycellulose (sodium CMC), polyvinylpyrrolidone (PVP), Konjac flour, carrageenan, xanthan gum, other hydrophilic polymers, or mixtures thereof. Viscosity modifiers can be used in conventional amounts and preferably in an amount of about 1 to about 40, and more preferably in an amount of about 2 to about 20 by weight of the dosage form.

Surfactants can be anything known to be used as surfactants. Some surfactants that may be useful in the present invention include, without limitation, various grades of the following commercial products: Arlacel®, Tween®, Capmul®, Centrophase®, Cremophor®, Labrafac®, Labrafil®, Labrasol®, Myverol®, Tagat®, and any non-toxic short and medium chain alcohols. Surfactants can be used in conventional amounts and preferably in an amount of about 0.01 to about 5, and more preferably in an amount of about 0.1 to about 2 by weight of the dosage form.

Buffers can be anything known to be used as a buffer. Some buffers that may be useful in the present invention include any weak acid or weak base or, preferably, any buffer system that is not harmful to the gastrointestinal mucosa. These include, but are not limited to, sodium carbonate, potassium carbonate, potassium carbonate, disodium hydrogen phosphate, sodium dihydrogen phosphate, and the equivalent potassium salts. Buffers can be used in conventional amounts and preferably in an amount of about 0.1 to about 10, and more preferably in an amount of about 1 to about 5 by weight of the dosage form.

Disintegrants which may be used include starch, cellulose, modified starch, microcrystalline cellulose, alginic acid, clays, veegum and super disintegrants including, without limitation, crosslinked PVP, croscaramellose salts such as croscaramellose sodium, starch derivatives like sodium starch glycolate.

Where such super disintegrants are used, they are traditionally found in an amount of between about 1 and about 20%, more preferably between about 2 and about 10%, and most preferably between about 2 and about 5% by weight of the finished dosage form. In addition to, instead of any portion of, or instead of any super disintegrant, the dosage forms in accordance with the present invention may include at least one effervescent couple or disintegrant.

Effervescent couples are made from a reaction of a soluble acid source and a metal carbonate or bicarbonate. The acid sources or acid may be any which are safe for human consumption and may generally include food acids, acid anhydrides and acid salts. Food acids include citric acid, tartaric acid, malic acid, fumaric acid, adipic acid, and succinic acids etc. Because these acids are directly ingested, their overall solubility in water is less important than it would be if the effervescent tablet formulations of the present invention were intended to be dissolved in a glass of water. Acid anhydrides and acid salts of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate. These effervescent couples may be provided in an amount of between about 3% and about 50% by weight of the dosage form, more preferably between about 3% and about 25% by weight.

Nonlimiting examples of such noneffervescent disintegration agents include: microcrystalline, cellulose, starches, corn starch, potato starch and modified starches thereof, clays, such as bentonite, alginates, gums such as agar, guar, locust bean, karaya, pecitin and tragacanth. These disintegrants may comprise up to about 20 weight percent and preferably between about 2% and about 10% of the total weight of the dosage form.

If desired the dosage form may also contain minor amounts of nontoxic substances such as wetting or emulsifying agents, pH buffering agents and the like, for example, sodium acetate, sorbitan monolaurate, triethanolamine, sodium acetate, triethanolamine oleate, sodium lauryl sulfate, dioctyl sodium sulfosuccinate, polyoxyethylene sorbitan fatty acid esters.

A mixture in accordance with this present invention is a blend of API containing particles, with or without other excipients or other particles. It is often, but not exclusively, a bulk material. A "dosage form" in accordance with the present invention is a tablet, capsule, caplet, sachet, powder or other solid known for the administration of medicines orally. It is generally made from a mixture as defined herein and is either formed (as in a tablet) or packaged (as in a capsule, powder, or sachet) into a form for use by a doctor or patient for administration. A tablet can be an ALKA-SELTZER®-like tablet which is dropped into a glass of a liquid and dissolved prior to ingestion, a dosage form which is orally disintegrable/dissolvable on a patient's tongue, a dosage form which is to be administered gingivally, buccally or sublingually, or a traditional dosage form which is to be swallowed as a dispersion, suspension or slurry. An orally disintegrable/dissolvable dosage form is one which is placed on the tongue and which dissolves/disintegrates in the mouth generally in about 90 seconds or less, more often in about 60 seconds or less. Thereafter, the resulting suspension, solution or slurry is swallowed. In buccal, gingival and sublingual dosage forms, the active ingredient is typically transferred through the oral mucosa. A dosage form could be prepared by metering powder or slugged cores into a hard gelatin capsule for oral ingestion or provided as a powder to be taken directly, to be sprinkled onto food, or mixed with a beverage prior to ingestion are also contemplated.

Dosage forms as contemplated by the present invention may be provided in a range of shapes and sizes. In a preferred embodiment, the dosage form is in a size capable of oral administration and provides a therapeutic amount of the API therein. Generally, such dosage forms will be less than 1.5 inches in any one direction, more preferably less than 1 inch and most preferably less than 0.75 inch. Shapes include but not limited to round with both flat or convex face, capsule shape (caplets), diamond shape, triangular, rectangular, hexagonal, pentagonal, heart-shaped, animal shaped tablets like rabbits, elephants etc. Dosage forms can be any size and shape, but preferable of a size and shape to avoid crushing or abuse.

The frequency of dosing depends on various factors including the amount of active ingredient present in the dosage form, the size of the dosage form, the weight of the patient, the condition of the patient, side effects of the active ingredient, etc. The administration of multiple dosage forms and multiple frequency of dosing is contemplated depending upon the above factors as well as duration of the patient's condition, how long the active ingredient stays in a patient's system, etc.

A further aspect of the present invention includes methods of making the CR coated particles described herein. As contemplated by this invention, the API particles and alternatively, at least one other ingredient, are combined with a solvent or a binder solution to form wet granulates. The wet granulates are subsequently milled and dried to a preferred average particle size of about 100 to 600, and more preferably about 150 to 500, and most preferably about 200 to about 400. In another preferred embodiment, the formed API containing particles preferably have a particle size distribution wherein no more than about 10% are less than 50 microns, and no more than 10% are larger than 700 microns. Of course, overs and unders could be discarded. Once the API or API containing particles have obtained the desired particle size, it is coated with one or more CR coatings via a standard coating method. This method may include spraying, dipping, wetting in a fluid bed, etc., to achieve a selected coating thickness. Other coatings may also be used over, under or between the CR coating(s). Once coated, the coated particle is allowed to set/dry so as to be stored and/or used in an end product.

Yet another aspect of the present invention includes methods of making dosage forms that include at least one granulate including wet granulate and/or CR coated particle as described herein. In one aspect, the dosage form is a tablet made by direct compression wherein the API particles (granulates or CR coated particles) are blended with at least one other ingredient. They may also be mixed with a second fat/wax-like particle as described herein. The blend is punched with steel punches to form the desired size and shape tablet. Hardness can range from 10-200 Newtons, more preferably 20-150 Newtons and friability should be less than 2%, preferably less than 1%. In another aspect, the dosage form is a capsule which may be dry filled. This form is made by filling the CR coated particles and optionally at least one other ingredient into a gelatin capsule.

The tablets of another embodiment of the invention often have a hardness of about 20 Newtons or less, more preferably about 10 to about 20 Newtons and a friability of more than 2% as measured by the U.S.P. method as of the filing date. Preferably these tablets are capable of rapidly disintegrating/dissolving in a patient's mouth in about 60 seconds or less, more preferably about 30 seconds or less as described above, such that the API containing particles can be swallowed as a dispersion, suspension or slurry.

Tablets can either be manufactured by direct compression, wet granulation, dry granulation or any other tablet manufacturing technique. See, e.g., U.S. Pat. Nos. 5,178,878, 5,223,264 and 6,024,981 which are incorporated by reference herein.

In another aspect, the present invention comprises an abuse resistant dosage form in accordance with the present invention and one or more indicia indicating that it is abuse resistant. In one embodiment, the dosage form itself includes the indicia. The indicia could be, for example, one or more letters such as "AR," one or more words such as "abuse" and/or "resistant" or a picture or symbol. These can be printed onto the surface of the dosage form, imbedded as a relief or as a raised structure. Instead, or in addition, the abuse resistant dosage forms of the present invention may be packaged in one or more blister packs, or in multi-tablet openable and reclosable containers, such as a bottle. The packaging, or any associated product label or package insert could also include one or more letters, words, pictures or symbols which indicate that the dosage forms were abuse resistant.

Such indicia could provide additional assistance in reducing abuse in a number of ways. For one thing, a patient who is informed of the abuse-resistant feature and insists on another form of the drug could alert a pharmacist that the patient could have a problem. Second, knowing that the dosage forms are abuse resistant could reduce their theft or their illegal resale as they would be less desirable to abusers.

EXAMPLES

Figure 2:
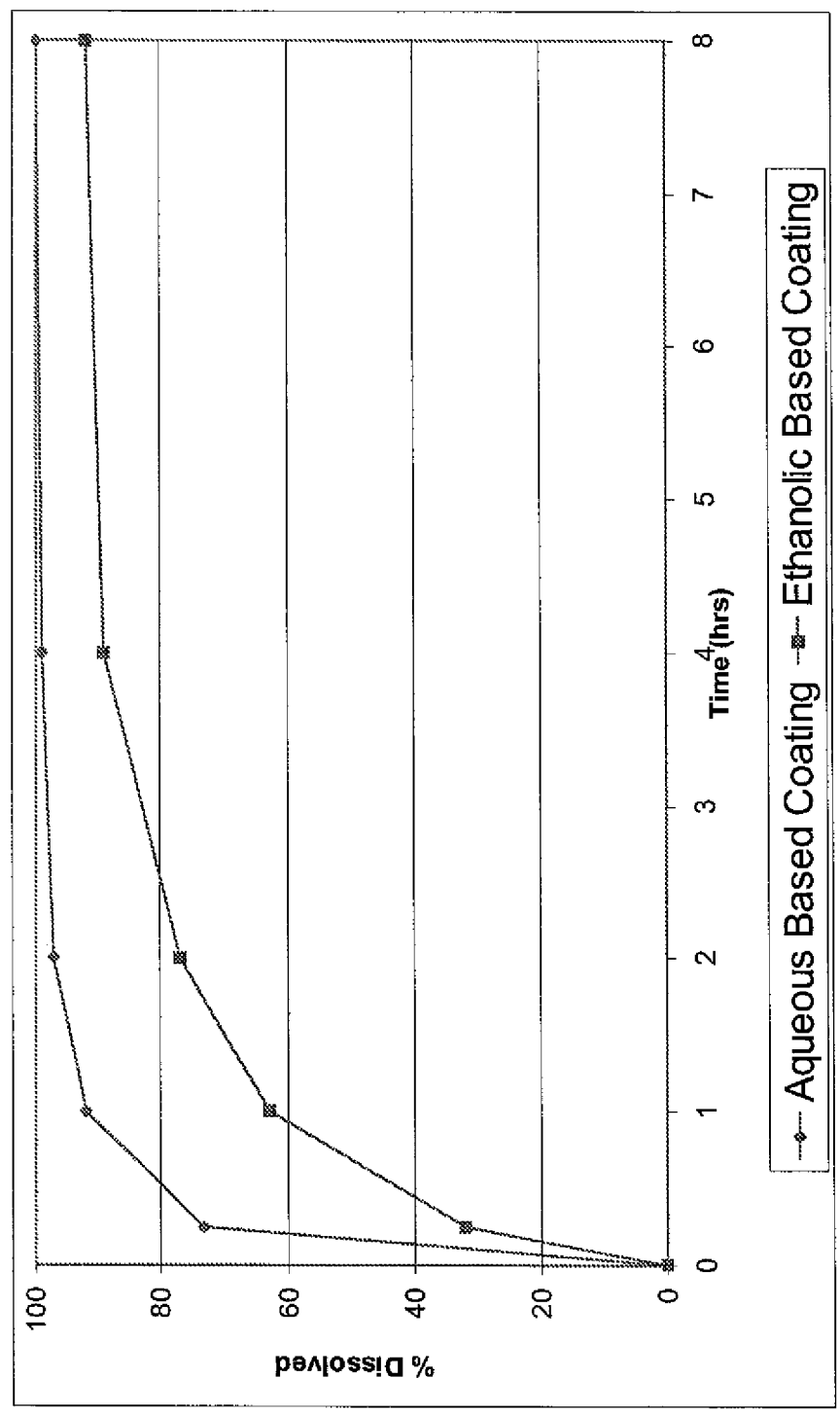
FIG. 2 illustrates comparative dissolution profiles for various coated granules with and without a crush resistant coating in accordance with Examples 1 and 2 of the present invention after crushing.

Example 1 [FIGS. 1 & 2 of 069]

The present invention can be illustrated by producing CR coated particles with wet granules as API particles.

TABLE 1

Granules Formulation

| Component | % (w/w) |
| --- | --- |
| Oxycodone Hydrochloride | 27.8 |
| Hydroxypropyl methylcellulose 844 | 46.3 |
| Ethylcellulose | 25.9 |

TABLE 2

Coated Granules Formulation

| Component | % (w/w) |
| --- | --- |
| Oxycodone Granules | 50.0 |
| Ethylcellulose | 33.3 |
| Magnesium Stearate | 16.7 |

Granules were manufactured in a high shear granulator where oxycodone hydrochloride, HPMC 844 and 71% of the total amount of ethylcellulose were dry mixed for 2 minutes. Then, a 10% hydro-ethanolic (30:70) solution of ethylcellulose was slowly added while maintaining the granulator impeller and chopper speeds at pre-selected values to provide enough shear for granule formation and growth. Solution addition was continued until the aforementioned percentage of ethylcellulose was realized. The granules were subsequently dried in a fluid bed to a level that renders them suitable for milling. The granules were then milled in a granumill and finally dried.

The prepared granules were then coated in a bottom spray fluid bed using a 15% alcoholic suspension of ethycellulose and magnesium stearate (2:1). Average particle size was determined by a sieve shaking method, and equaled about 630 microns. This is the geometric mean diameter, the number 630 was obtained by manually plotting the cumulative % frequency against the particle size on a Log-probability paper. The dissolution profile of these coated granulates were tested (FIG. 1).

Three aliquots of a sample were crushed using a mortar and pestle, crushing in 12 circular strokes of the pestle. The aliquots were pooled and then divided and tested for dissolution in 500 mL of medium (0.1N HCl). At specified time points, 5 mL aliquots were pulled from each vessel and analyzed via HPLC versus a standard. The results are shown in FIG. 1 for the uncrushed coated particles and FIG. 2 for the "crushed" coated particles and in both plots, the dark squares indicate the measured data points.

Example 2 [FIGS. 1 & 2 of 069]

The methods of making coated particles, described above in Example 1 were employed again except the formulation was coated with the aqueous EC dispersion.

TABLE 3

Granules Formulation

| Component | % (w/w) |
| --- | --- |
| Oxycodone Hydrochloride | 27.8 |
| Hydroxypropyl methylcellulose 844 | 46.3 |
| Ethylcellulose | 25.9 |

TABLE 4

Coated Granules Formulation

| Component | % (w/w) |
| --- | --- |
| Oxycodone Granules | 50.0 |
| Surelease ® (25% Solid) | 50.0 |

The coating used was a SURELEASE aqueous dispersion (Commercial Aqueous dispersion of EC from Colorcon Manufacturer Lot #1N509251) The dissolution results of uncrushed (FIG. 1) and crushed (FIG. 2) particles from the aqueous coating are shown in plots using diamonds indicating the measured data points.

Example 3 [From 069]

TABLE 5

Granules Formulation

| Component | % (w/w) |
| --- | --- |
| Oxycodone Hydrochloride | 46.1 |
| Hydroxypropyl methylcellulose 844 | 36.9 |
| Ethylcellulose | 17.0 |

TABLE 6

Coated Granules Formulation

| Component | % (w/w) |
| --- | --- |
| Oxycodone Granules | 50.0 |
| Ethylcellulose | 33.3 |
| Magnesium Stearate | 16.6 |

The same manufacturing method as used in Example 1 can be used except only 54% of EC is dry mixed with other ingredients instead of 71%.

Example 4 [From 069]

TABLE 7

Granules Formulation

| Component | % (w/w) |
| --- | --- |
| Oxycodone Hydrochloride | 46.1 |
| Hydroxypropyl methylcellulose 844 | 36.9 |
| Ethylcellulose | 17.0 |

TABLE 8

Coated Granules Formulation

| Component | % (w/w) |
| --- | --- |
| Oxycodone Granules | 50.0 |
| Ethylcellulose | 32.3 |
| Lutrol F127 | 1.6 |
| Magnesium Stearate | 16.1 |

The same manufacturing method as in Example 1 may be used except only 54% of EC is mixed dry with other ingredients (instead of 71). Also the coating dispersion contained EC and additives, namely: magnesium stearate:Lutrol:Ethanol ratio of 10:5:0.5:84.5.

Figure 3:
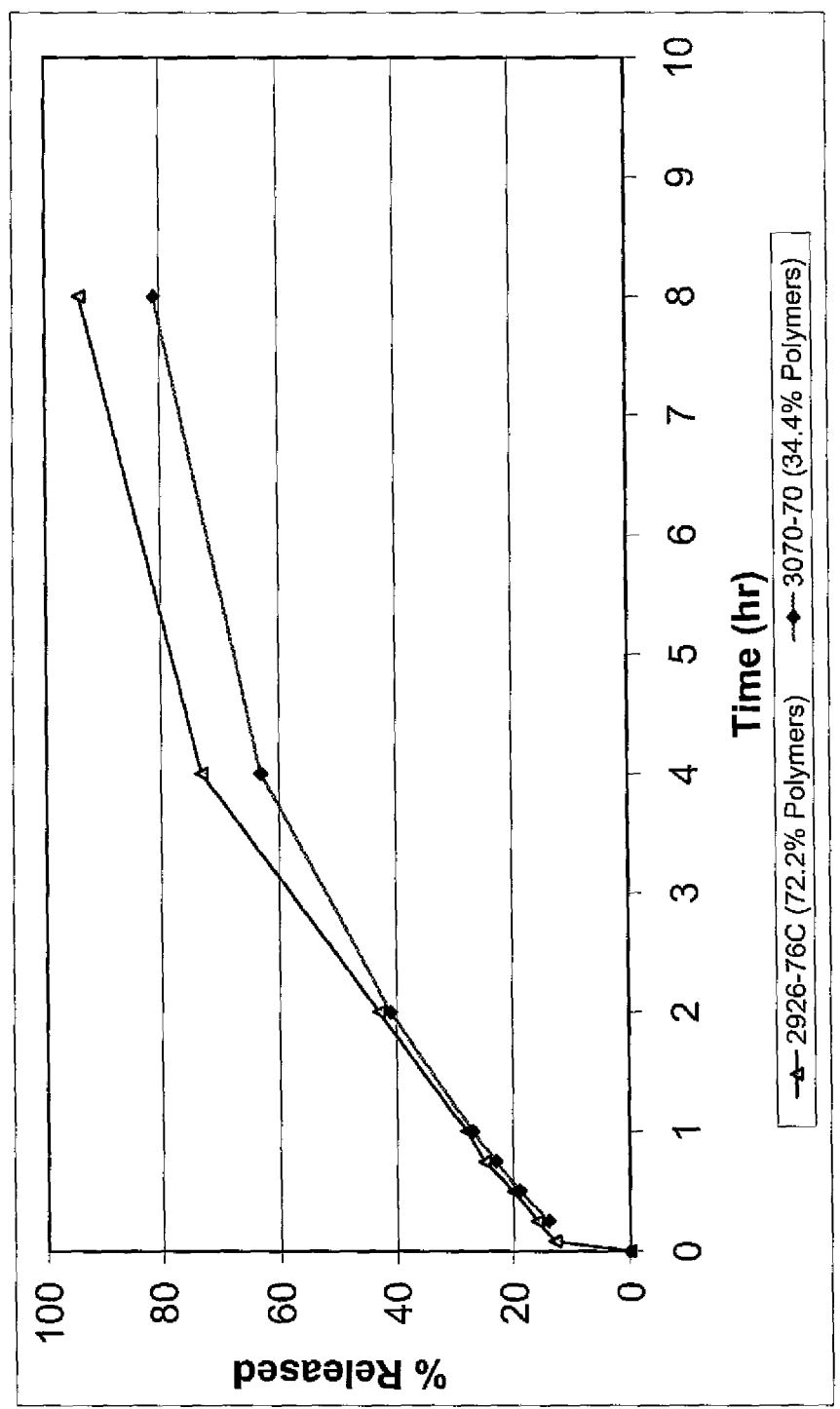
FIG. 3 illustrates the dissolution profiles of CR coated granulates of Examples 1 and 5 of the invention containing different levels of polymer in the granulate.
Figure 4:
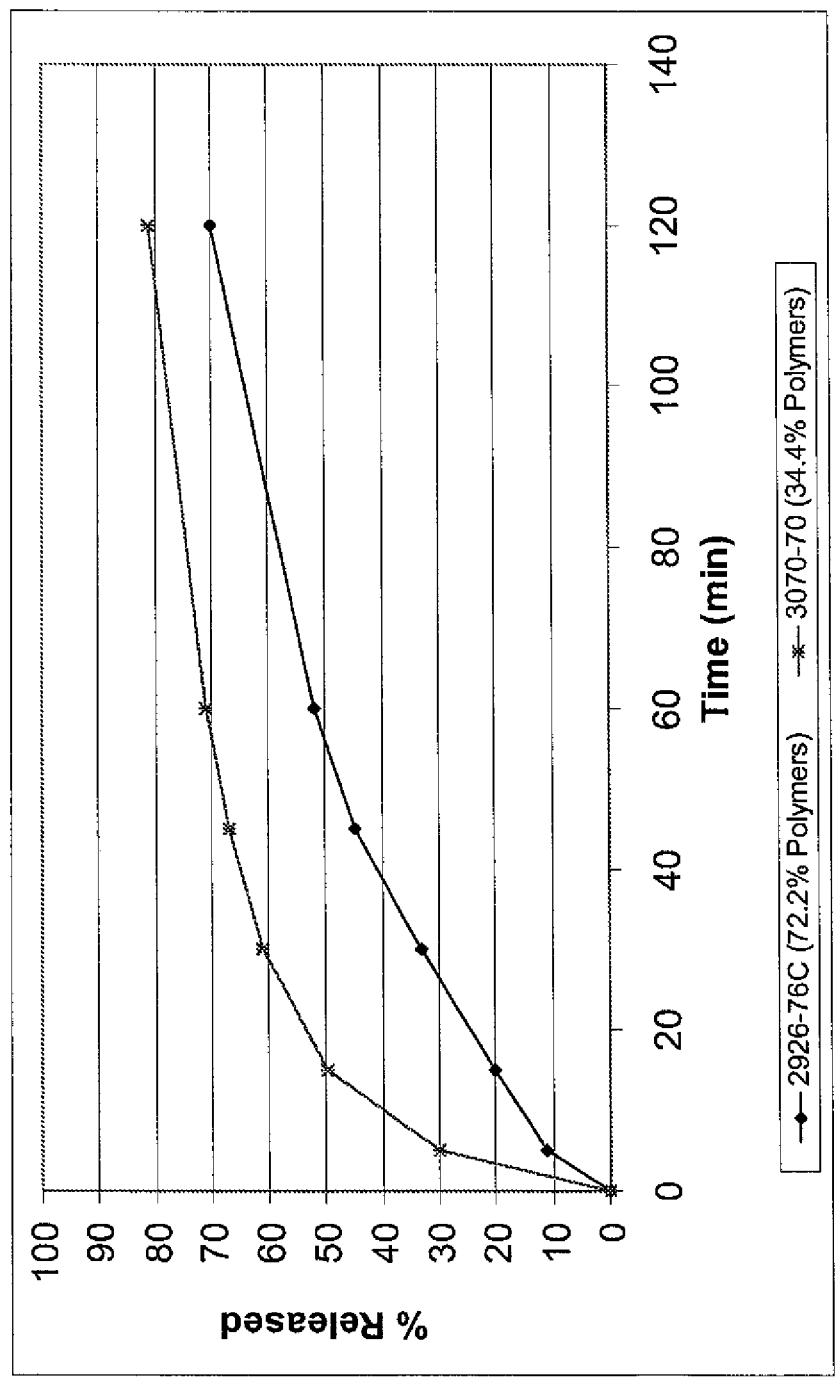
FIG. 4 illustrates the dissolution profiles of CR coated granulates of Examples 1 and 5 of the invention containing different levels of polymer in the granulate after crushing.

Example 5 [FIGS. 3 & 4 from 069]

TABLE 9

Granules Formulation

| Component | % (w/w) |
| --- | --- |
| Oxycodone Hydrochloride | 65.6 |
| Hydroxypropyl methylcellulose 844 | 22.5 |
| Ethylcellulose | 11.9 |

TABLE 10

Coated Granules Formulation

| Component | % (w/w) |
| --- | --- |
| Oxycodone Granules | 50.0 |
| Ethylcellulose | 33.3 |
| Magnesium Stearate | 16.7 |

The same manufacturing method used as in Example 1 was employed here except only 47% of EC was dry mixed with other ingredients instead of 71% in the granulate core. FIGS. 3 and 4 provide dissolution profiles in 0.1N HCl for 50% coated granules with different levels of polymers in the granule portion of the coated granule. FIG. 3 illustrates a comparison between the dissolution profiles of the granules in Example 1, which contained approximately 72.2% polymer, coated in an ethanol based EC coating, with the coated particles produced in accordance with this example (Example 5) where the granulate (the uncoated granulate) contained approximately 34.4% polymer, coated with the same ethanolic based EC coating. FIG. 4 demonstrates the dissolution profiles of the same materials after they have been crushed as described in Example 1. In FIG. 3, the unshaded triangles represent the data plotted for the granulate of Example 1 and the shaded diamonds for the coated granulate of Example 5. In FIG. 4, the shaded diamonds provide the data for the coated granulate of Example 1 and the asterisks provide the data for the coated granulate of Example 5. It will be noted from FIG. 4 that the higher level of polymer content in the core (72.2% as opposed to 34.4%) provided relatively better crush resistance.

Example 6 [FIG. 1 from 074 App]

The same manufacturing method as in Example 1 was employed here except that here the API particles were mixed with barrier beads as discussed herein.

TABLE 11

Granules Formulation

| Component | % (w/w) |
| --- | --- |
| Oxycodone Hydrochloride | 27.8 |
| Hydroxypropyl methylcellulose 844 | 46.3 |
| Ethylcellulose | 25.9 |

TABLE 12

Coated Granules Formulation

| Component | % (w/w) |
| --- | --- |
| Oxycodone Granules | 50.00 |
| Ethylcellulose | 33.33 |
| Magnesium Stearate | 16.67 |

Figure 5:
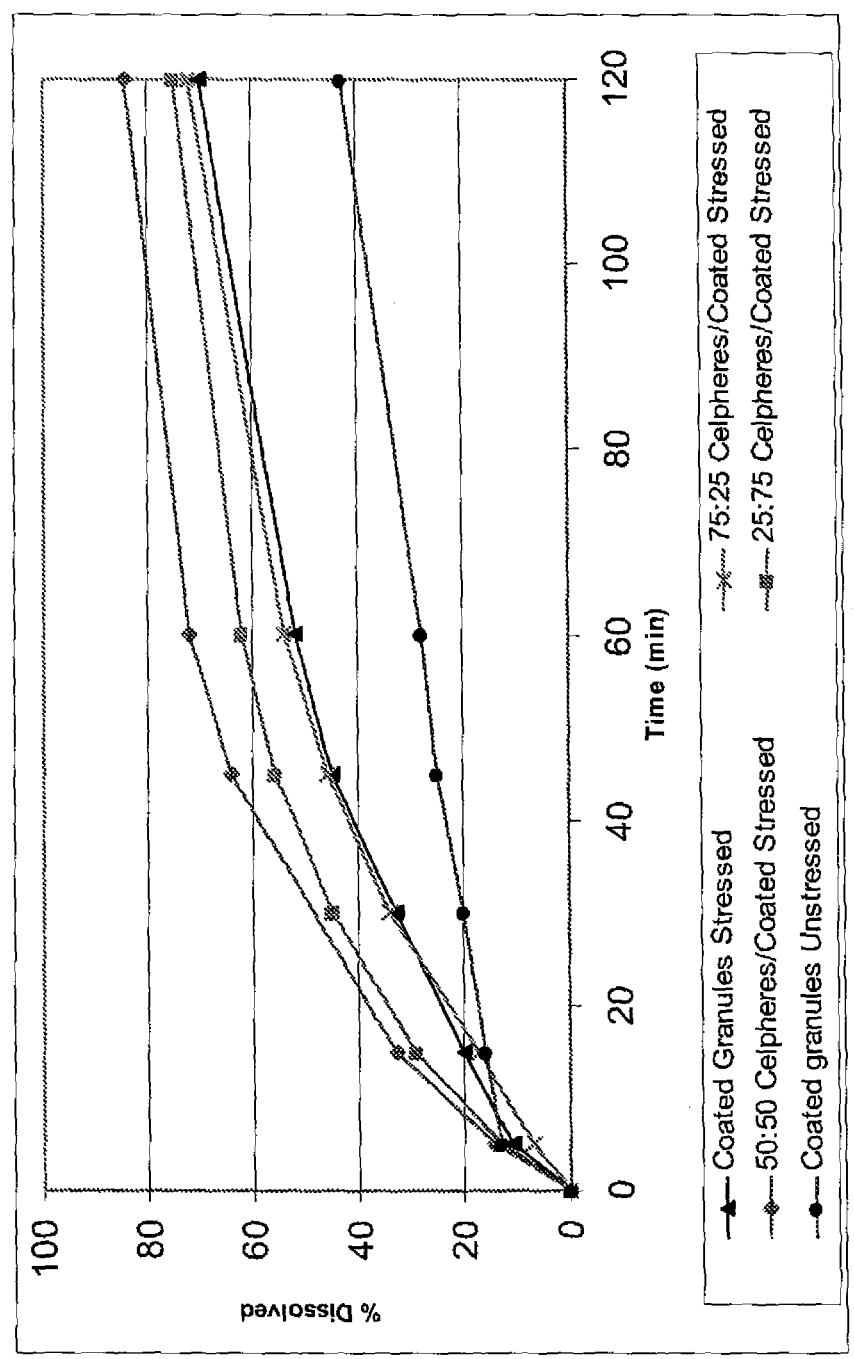
FIG. 5 illustrates comparative dissolution results for various coated granulates with and without barrier beads in variant proportions. The line formed by the triangles represents coated granules alone; the line formed by the diamonds represents a 50:50 mixture of celpheres and coated granulate produced in Example 6; the line formed by the "x"s represents a 75:25 mixture of celpheres to the coated granules; and the line formed by the squares represents a 25:75 mixture of celpheres to the coated granules of Example 6.

The coated granulates and barrier beads are then mixed in different proportions. Microcrystalline cellulose particles commercially available as Celphere CP-507 were used. Specifically, the coated particles were mixed with CP-507 at 25:75, 50:50 and 75:25. Published size information for the CP-507 was at least about 75% within range of 500-710 microns. The mixtures were subjected to mechanical stress by using 130 mm OD Porcelain mortar and 1-pound pestle. In summary, the mixtures were subjected to 12 strokes with the pestle each stroke included a pounding motion followed by a horizontal fully circled abrasive motion. Oxycodone release from the stressed granules was measured in USP Dissolution apparatus 2 using 0.1N HCl as release medium. The release profiles from non-stressed as well as stressed mixtures of oxycodone coated granules and Celpheres are presented in FIG. 5.

Note that at 75:25 barrier bead:API particle ratio, additional protection was obtained against stress. In other instances, the ratio needed to provide additional protection when compared to a formulation without barrier beads will differ. It is also important to note that this improvement was realized using protected particles which were themselves designed to be crush resistant. Indeed, granulates made with certain celluloses from an aqueous/alcoholic solution as a binder has been found to provide crush resistance when compared to an identical granulate made using water without alcohol as the binder. Similarly, a particle coated with a cellulose from an aqueous/alcoholic solution has been found to independently provide crush resistance when compared to an identically coated particle made using water without alcohol for the coating. Both of these discoveries are the subject of concurrently filed patent applications. Thus, the example demonstrates improvements resulting from the use of barrier beads can be obtained even when combined with other crush resistant technology. Indeed, improvement was realized here even where the average particle size of the barrier beads was considered to be less than that of the protected particles.

Example 7 [FIG. 2 from 074 App] [Negative Example???]

Figure 6:
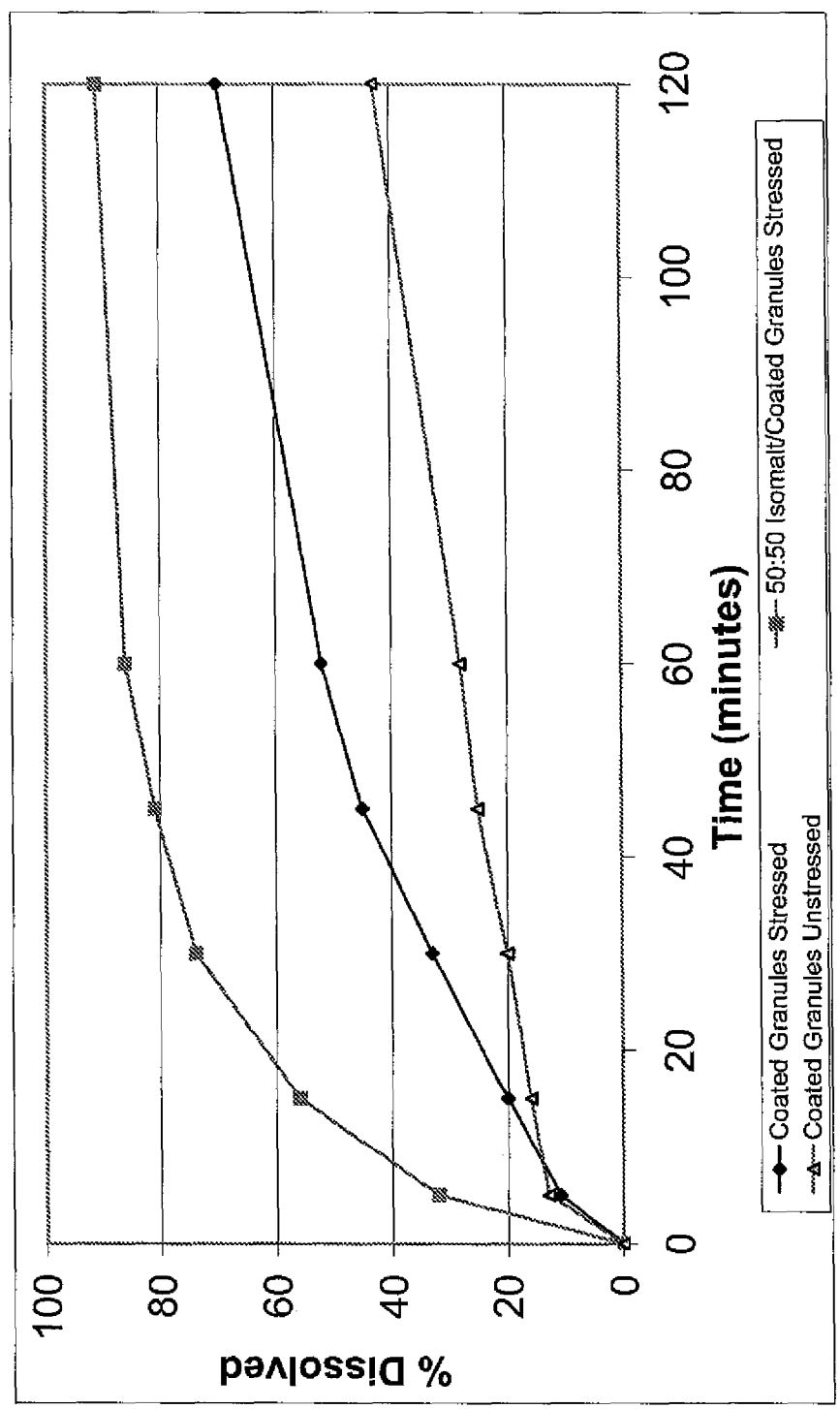
FIG. 6 illustrates a comparative test undertaken with the materials described in Example 7.

The coated oxycodone granules described in Example 6 above were also mixed in a 50:50 mixture with isomalt granules manufactured in Fluid bed granulator as barrier beads. The granules mixture was stressed in a mortar and pestle as described in example 6 above. The release profiles from nonstressed as well as stressed mixtures of oxycodone coated granules and isomalt granules are presented in FIG. 6.

Example 8 [From 077] [Repetitive of Ex. 1, Removed]

[Watch to Change all Table Numbers, and Possibly Figure Numbers as Well]

Example 9 [From 078]

Granules can be manufactured using a high shear granulator wherein oxycodone hydrochloride, hydroxymethylcellulose HPMC 844, and from about 47% to about 54% of the total amount of ethylcellulose to be used are dry mixed for a period of 2 minutes. Then, a 10% hydro-ethanolic (30:70) solution of ethylcellulose can be slowly added while maintaining the granulator impeller and chopper speeds at preselected values sufficient to provide shear for granule formation and growth. The solution can be added until the desired percentage ethylcellulose is obtained. The granules can then be dried in a fluid bed to a level rendering them suitable for milling. The granules can then be milled in a mill and dried.

Using a process similar to that described hereinabove and using 54% of the total amount of ethylcellulose, the following uncoated granulate composition was prepared:

TABLE 16

| Uncoated Oxycodone Granule | |
| --- | --- |
| Ingredient | Amount (% w/w) |
| Oxycodone HCl | 46.1 |
| Hydroxypropyl methylcellulose (HPMC) | 36.9 |
| Ethylcellulose | 17.0 |
| Total | 100.0 |

The prepared granules can then be coated in a bottom spray fluid bed using a 15% alcoholic suspension of ethylcellulose and magnesium stearate (2:1). After coating, about 40% of the coated granules based on weight can be composed of the coating materials. Using this process, the following coated granule formulation was prepared:

TABLE 17

| Coated Oxycodone Granule | |
| --- | --- |
| Ingredient | Amount (% w/w) |
| Oxycodone granules (Oxycodone HCl, HPMC, ethylcellulose of Table 16) | 60.00 |
| Ethylcellulose | 26.67 |
| Magnesium stearate | 13.33 |
| Total | 100.00 |

Example 10 [From 078]

Coated granules prepared as described herein above can be formed into solid dosage form, e.g., tablet. The coated granules can be mixed with EMCOMPRESS (dibasic calcium phosphate dehydrate), lactose (FAST-FLO, spray-dried), COMPRITOL ATO 888 (glyceryl behenate) in a V-blender for a period of about 30 minutes. The blended mixture can then be compressed in a rotary tablet press to form tablets. Tablet weight can vary from about 110 mg for a 10 mg oxycodone HCl active ingredient to about 880 mg for an 80 mg oxycodone HCl tablet. Using this process, the following tablet was prepared:

TABLE 18

| Oxycodone HCl (10 mg) Tablet Formulation | | |
| --- | --- | --- |
| Component | Amount (% w/w) | Amount (mg) |
| Oxycodone coated granules (Table 17) | 38.82 | 42.70 |
| EMCOMPRESS | 33.18 | 36.50 |
| Lactose | 23.00 | 25.30 |
| COMPRITOL (glyceryl behenate) | 5.00 | 5.50 |
| Total | 100.00 | 110.00 mg |

The above calculations account for the fact that the actual potency of the coated granules made were less than the theoretical amount. Thus, 110.00 mg of the prepared tablet contained 10 mg oxycodone HCl.

Various tablet shapes and sizes can be employed with the invention. Furthermore, the same process above can be used except the second particle fat/wax with a low melting point is melted and poured into a capsule shell and combined, or pre-combined, and the suspension can then be poured into a capsule shell.

Example 11 [From 078—FIG. 1]

10 mg oxycodone HCl tablets prepared according to the invention were dissolved in two dissolution medium: acid/water medium (normal) and water/alcohol (alcohol) medium in order to measure the percent active ingredient released over time and compare the results.

Using compressed tablets prepared using the 10 mg oxycodone-containing composition prepared according to Example 10 with the formulation of Table 18, the normal dissolution of the active ingredient in dissolution medium was measured. Starting with 500 ml 0.1N HCl (in water) as a release (dissolution) medium at a temperature of 37° C. in a USP Dissolution apparatus (2 paddles at a rate of rpm 50), granules (equivalent to 10 mg oxycodone HCl) were added to the dissolution medium. Samples were withdrawn at intervals 5 min, 15 min, 30 min, 45 min, 60 min, 120 min. Each sample was tested for solubilized oxycodone content using HPLC method, and the values described in percentage terms and plotted against time to establish release profiles. The data appears in the following table:

TABLE 19

Percent (%) Oxycodone Released per Time
in HCl/Water Dissolution Medium

| Time (min) | Percent (%) Release Oxycodone HCl |
|---|---|
| 0 | 0 |
| 5 | 2 |
| 15 | 10 |
| 30 | 22 |
| 45 | 33 |
| 60 | 44 |
| 120 | 82 |

Figure 7:
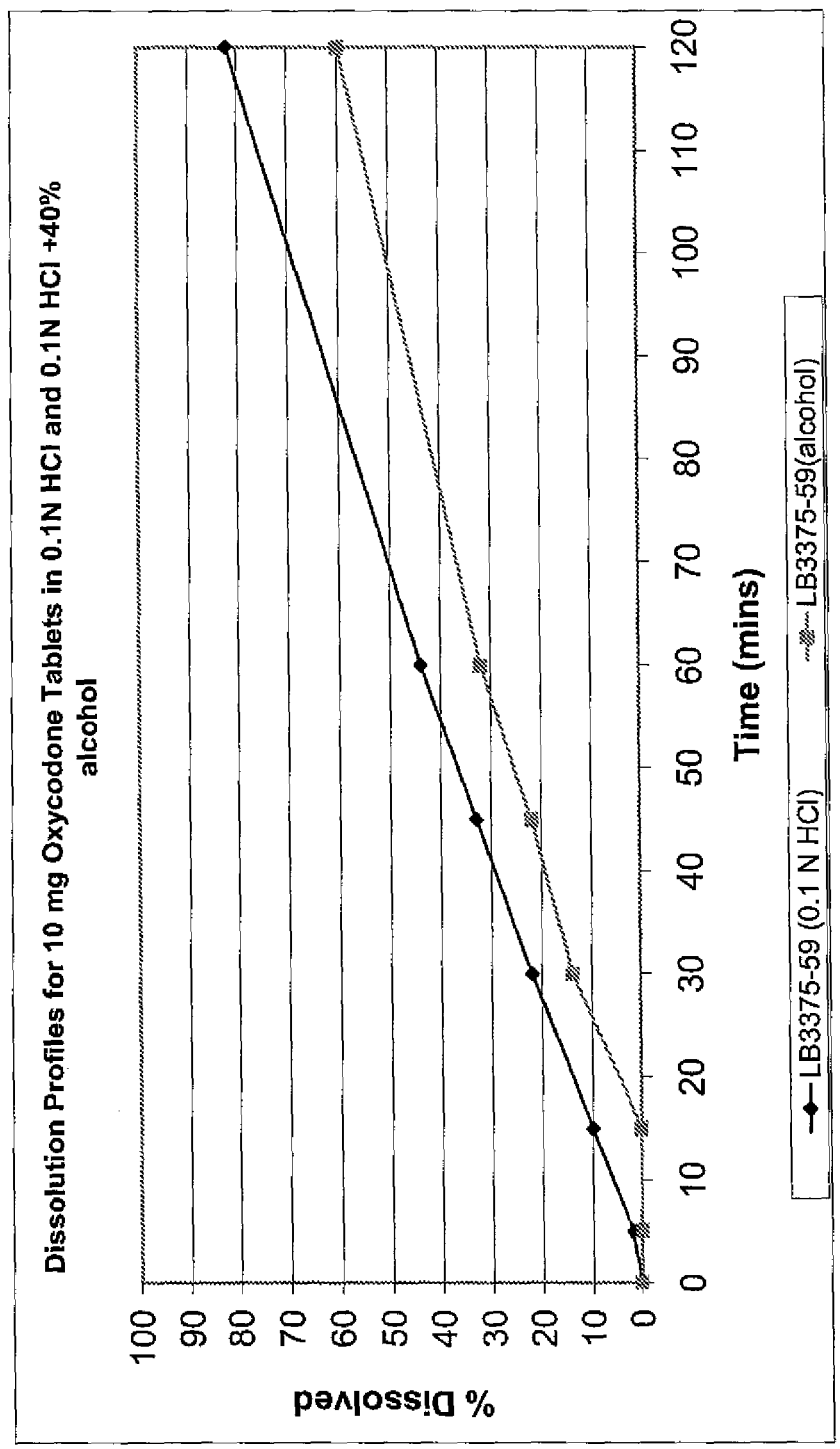
FIG. 7 is a chart showing the comparative dissolution profiles as described in Example 11 for oxycodone HCl (10 mg) tablets prepared according to one embodiment of the invention.

The normal dissolution data as plotted appears in FIG. 7.

Normal dissolution was compared to dissolution conditions representative of solvent (alcohol)-accelerated dose dumping abuse and tampering conduct. The procedure above was repeated except the dissolution medium contained water:ethanol in 60:40 volume ratio simulating a combination of the tablet with alcohol. Samples were taken at 5, 15, 30, 45, 60 and 120 minute intervals, and measured again for oxycodone content. The results were plotted against time and appear in the following table:

TABLE 20

Percent (%) Oxycodone Released per Time
in Alcohol and Water Dissolution Medium

| Time (min) | Percent (%) Release Oxycodone HCl |
|---|---|
| 0 | 0 |
| 5 | 0 |
| 15 | 0 |
| 30 | 14 |
| 45 | 22 |
| 60 | 32 |
| 120 | 60 |

The data as plotted appears in the chart of FIG. 7 (Dissolution Profiles).

As can be seen from the figure, the ability to accelerate the release of active ingredients (e.g. oxycodone HCl) from tablet dosage forms prepared according to the invention, using alcohol as a solvent, is limited. The measured amounts of oxycodone active release in alcohol-containing dissolution medium is comparable to that amount measured in the acidic water-containing (normal) dissolution medium.

Example 12 [From 078]

Using a process similar to that described above in Example 9 and using 54% of the total amount of ethylcellulose, the following uncoated granulate composition was prepared:

TABLE 21

Uncoated Oxycodone Granule

| Ingredient | Amount (% w/w) |
|---|---|
| Oxycodone HCl | 65.61 |
| Hydroxypropyl methylcellulose (HPMC) | 22.49 |
| Ethylcellulose | 11.90 |
| Total | 100.00 |

Using a process similar to that described above in Example 9, the following coated granule composition was prepared:

TABLE 22

Coated Oxycodone Granule

| Ingredient | Amount (% w/w) |
|---|---|
| Oxycodone granules (oxycodone HCl, HPMC, ethylcellulose of Table 21) | 50.00 |
| Ethylcellulose | 33.33 |
| Magnesium stearate | 16.67 |
| Total | 100.00 |

Using a process similar to that described above in Example 10, the following formulation was prepared:

TABLE 23

Oxycodone HCl (80 mg) Tablet Formulation

| Ingredient | Amount (% w/w) | Amount (mg) |
|---|---|---|
| Oxycodone coated granules (of Table 22) | 39.02 | 243.90 |
| EMCOMPRESS | 30.59 | 191.20 |
| Lactose | 20.38 | 127.40 |
| COMPRITOL (glyceryl behenate) | 10.00 | 62.50 |
| Total | 100.00 | 625.00 mg |

Example 13 [From 078—FIG. 2]

80 mg oxycodone HCl tablets prepared according to the invention and as formulated in Table 23, were dissolved in two dissolution medium: acid/water medium (normal) and water/alcohol (alcohol) medium in order to measure the percent active ingredient released over time and compare the results.

Using compressed tablets prepared using the 80 mg oxycodone-containing composition prepared according to Example 12 with the formulation of Table 23, the normal dissolution of the active ingredient in solution medium was measured. Starting with 500 ml 0.1N HCl (in water) as a release (dissolution) medium at a temperature of 37° C. in a USP Dissolution apparatus (2 paddles at a rate of rpm 50), granules (equivalent to 80 mg oxycodone HCl) were added to the dissolution medium. Samples were withdrawn at intervals 5 min, 15 min, 30 min, 45 min, 60 min, 120 min. Each sample was tested for solubilized oxycodone content using HPLC method, and the values described in percentage terms and plotted against time to establish release profiles. The data appears in the following table:

TABLE 24

Percent (%) Oxycodone Released per Time in Acid/Water Dissolution Medium

| Time (min) | Percent (%) Release oxycodone HCl |
|---|---|
| 0 | 0 |
| 5 | 1 |
| 15 | 2 |
| 30 | 4 |
| 45 | 6 |
| 60 | 8 |
| 120 | 18 |

Figure 8:
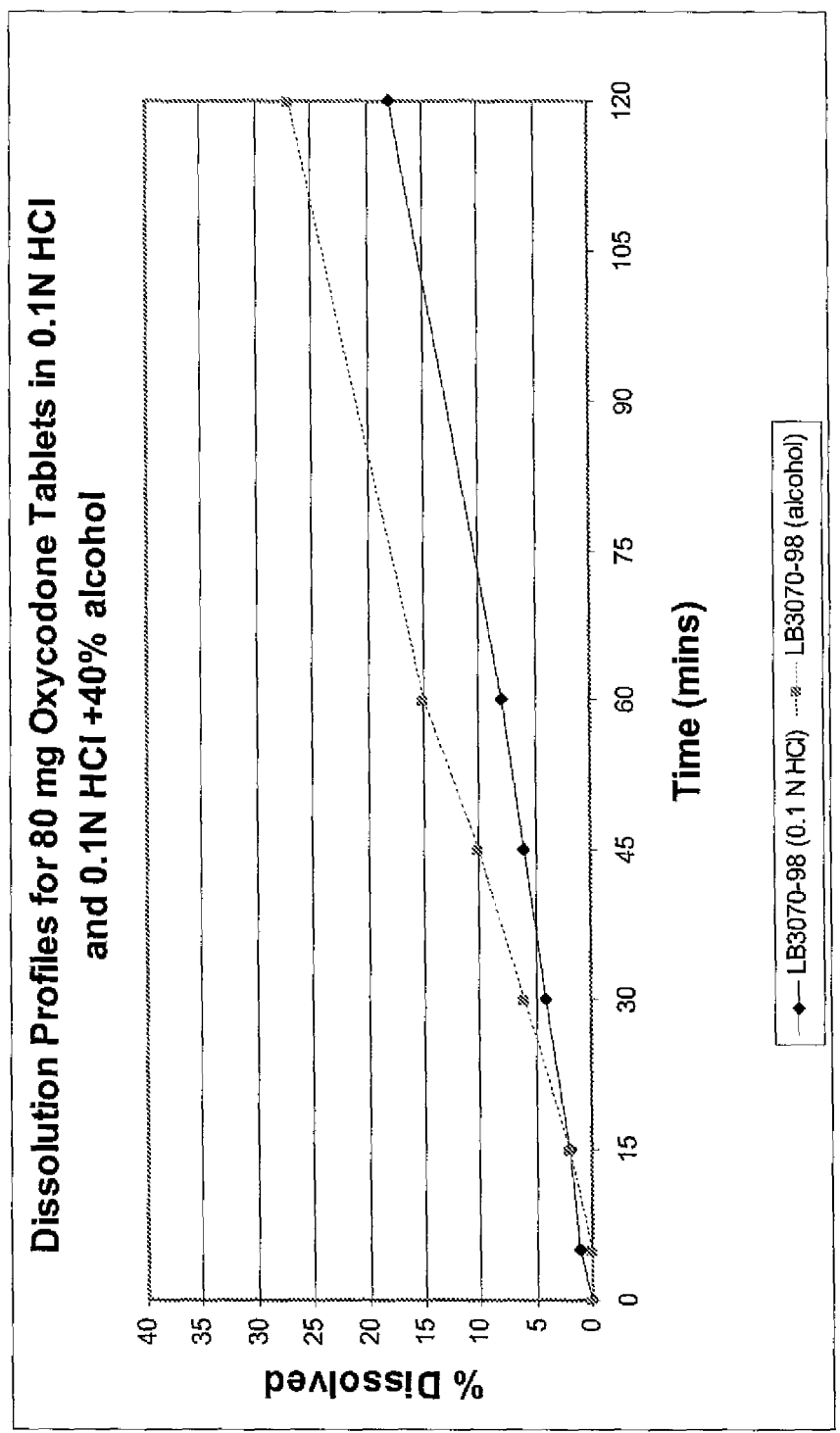
FIG. 8 is a chart showing the comparative dissolution profiles as described in Example 13 for oxycodone HCl (80 mg) tablets prepared according to one embodiment of the invention.

The normal dissolution data as plotted appears in FIG. 8.

Normal dissolution was compared to dissolution conditions representative of solvent (alcohol)-accelerated dose dumping abuse and tampering conduct. The procedure above was repeated except the dissolution medium contained water:ethanol in 60:40 volume ratio simulating a combination of the tablet with alcohol. Samples were taken at 5, 15, 30, 45, 60 and 120 minute intervals, and measured again for oxycodone content. The results were plotted against time and appear in the following table:

TABLE 25

Percent (%) Oxycodone Released per Time in Water/Alcohol Dissolution Medium

| Time (min) | Percent (%) Release Oxycodone HCl |
|---|---|
| 0 | 0 |
| 5 | 0 |
| 15 | 2 |
| 30 | 6 |
| 45 | 10 |
| 60 | 15 |
| 120 | 27 |

The alcohol dissolution data as plotted appears in FIG. 8. As can be seen from the chart of FIG. 8, the ability to accelerate the release of active ingredients (e.g. oxycodone HCl) from tablet dosage forms prepared according to the invention, using alcohol as a solvent, is limited. The measured amounts of oxycodone active release in alcohol-containing dissolution medium is at least comparable to that amount measured in the acidic water-containing (normal) dissolution medium.

Example 14

The present invention can be illustrated by producing a composition including CR coated particles with wet granules as API particles.

Using a process similar to that described above in Example 1, except 53% of EC is dry mixed with other ingredients instead of 71%, the following formulation was prepared, which differs from Example 1 in the amounts of each component used:

TABLE 26

| Granules Formulations | |
|---|---|
| Ingredient | Amount (% w/w) |
| Oxycodone HCl | 46.1 |
| Hydroxypropyl methylcellulose (HPMC) | 36.9 |
| Ethylcellulose | 17.0 |
| Total | 100.00 |

TABLE 27

| Coated Granules Formulation | |
|---|---|
| Ingredient | Amount (% w/w) |
| Oxycodone granules (oxycodone HCl, HPMC, ethylcellulose) | 60.00 |
| Ethylcellulose | 26.67 |
| Magnesium stearate | 13.33 |
| Total | 100.00 |

Using a process similar to that described above in Example 10, the following formulation was prepared using different amounts and components than in Example 10:

TABLE 28

| Oxycodone HCl (80 mg) Tablet Formulation | | |
|---|---|---|
| Component | Amount (% w/w) | Amount (mg) |
| Oxycodone coated granules | 33.98 | 288.8 |
| Lactose Monohydrate (fast Flo) | 56.02 | 476.2 |
| COMPRITOL (glyceryl behenate) | 10.00 | 85.0 |
| Total | 100.00 | 850.0 mg |

While COMPRITOL is always kept at 10% of the total weight of the dosage form (tablet), any change in the actual assay amount, from theoretical values, is accounted for by changing the amount of lactose and coated granules to maintain the amount of Oxycodone HCl at 80 mg per tablet. The average tablet weight is 850 mg, and has an average hardness of between 140 and 155 N. The tablet dimensions are 0.3125"×0.5625".

Using a process similar to that of Example 11, the following data was obtained using the above formulation:

TABLE 29

Percent (%) Oxycodone Released per Time in HCl/Water Dissolution Medium

| Time (min) | Percent (%) Release Oxycodone HCl |
|---|---|
| 0 | 0 |
| 30 | 11 |
| 60 | 28 |
| 120 | 62 |
| 240 | 95 |
| 360 | 97 |
| 480 | 98 |
| 600 | 98 |
| 720 | 99 |

TABLE 30

Percent (%) Oxycodone Released per Time in Alcohol and Water Dissolution Medium

| Time (min) | Percent (%) Release Oxycodone HCl |
|---|---|
| 0 | 0 |
| 5 | 0 |
| 15 | 3 |
| 30 | 7 |
| 45 | 11 |
| 60 | 14 |
| 120 | 31 |

TABLE 31

Percent (%) Oxycodone Released per Time in HCl/Water Dissolution Medium after crushing

| Time (min) | Percent (%) Release Oxycodone HCl |
|---|---|
| 0 | 0 |
| 5 | 8 |
| 15 | 34 |
| 30 | 69 |
| 45 | 86 |
| 60 | 94 |
| 120 | 98 |

Figure 9:
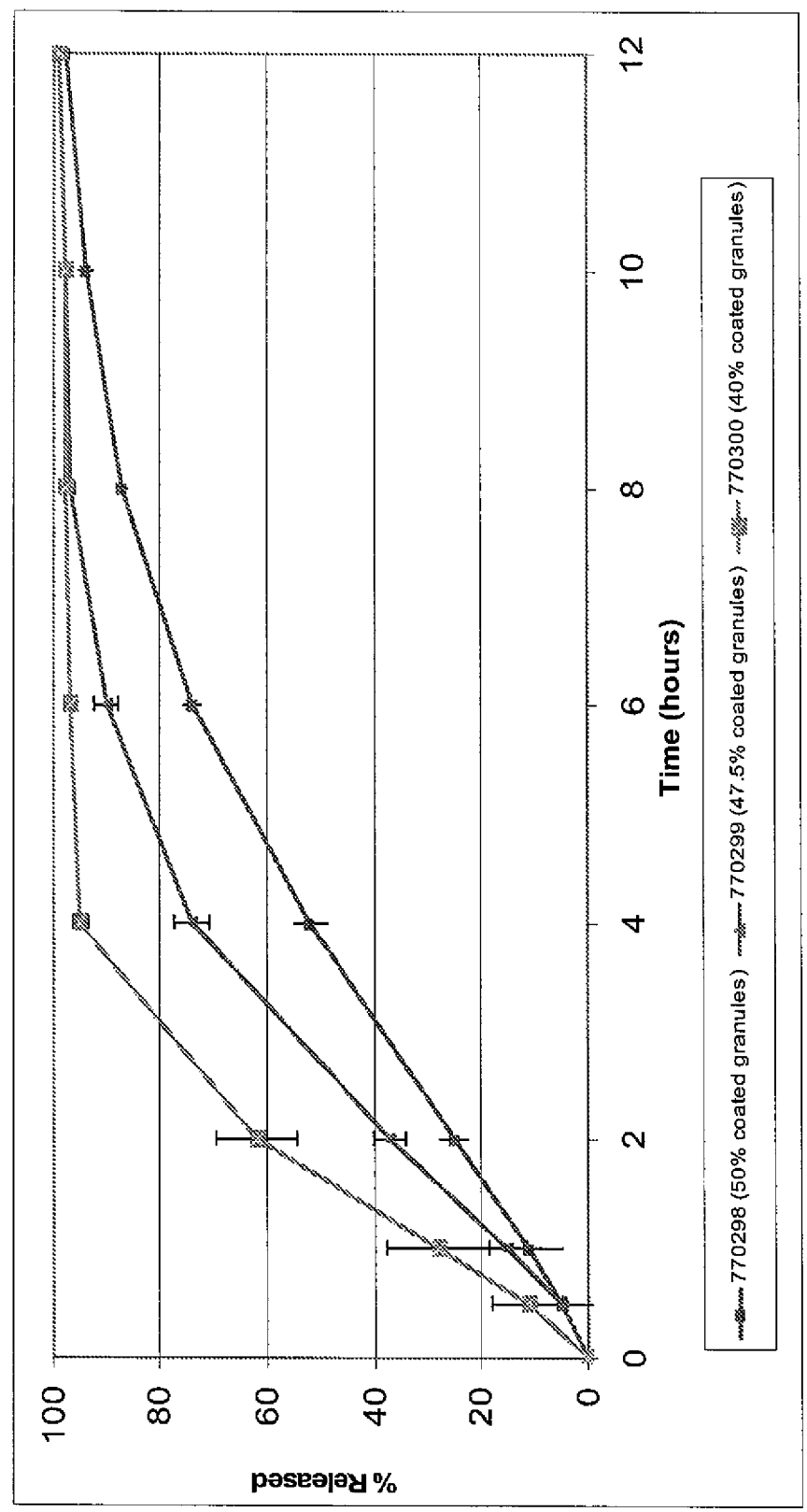
FIG. 9 is a chart showing the comparative dissolution profiles of CR coated granulates of Examples 14 through 16 of the invention containing different percentages of coated granulate.

The data of Table 29 is illustrated in FIG. 9 as the upper curve with shaded squares and "X"'s.

Example 15

Using a process similar to that described above in Example 14, again dry mixing only 53% of EC with other ingredients, the following formulation was prepared, which differs from Example 14 in the amounts of each component used:

TABLE 32

Granules Formulations

| Ingredient | Amount (% w/w) |
|---|---|
| Oxycodone HCl | 46.1 |
| Hydroxypropyl methylcellulose (HPMC) | 36.9 |
| Ethylcellulose | 17.0 |
| Total | 100.00 |

TABLE 33

Coated Granules Formulation

| Ingredient | Amount (% w/w) |
|---|---|
| Oxycodone granules (oxycodone HCl, HPMC, ethylcellulose) | 52.5 |
| Ethylcellulose | 31.7 |
| Magnesium stearate | 15.8 |
| Total | 100.00 |

Using a process similar to that described in Example 14, the following formulation was prepared using different amounts than in Example 14:

TABLE 34

Oxycodone HCl (80 mg) Tablet Formulation

| Component | Amount (% w/w) | Amount (mg) |
|---|---|---|
| Oxycodone coated granules | 38.89* | 330.6 |
| Lactose Monohydrate (fast Flo) | 51.11 | 434.4 |
| COMPRITOL (glyceryl behenate) | 10.00 | 85.0 |
| Total | 100.00 | 850.0 mg |

While COMPRITOL is always kept at 10% of the total weight of the dosage form (tablet), any change in the actual assay amount, from theoretical values, is accounted for by changing the amount of lactose and coated granules to maintain the amount of Oxycodone HCl at 80 mg per tablet. The average tablet weight is 850 mg, and has an average hardness of between 140 and 155 N. The tablet dimensions are 0.3125"×0.5625".

Using a process similar to that of Example 14, the following data was obtained using the above formulation:

TABLE 35

Percent (%) Oxycodone Released per Time in HCl/Water Dissolution Medium

| Time (min) | Percent (%) Release Oxycodone HCl |
|---|---|
| 0 | 0 |
| 30 | 5 |
| 60 | 15 |
| 120 | 37 |
| 240 | 74 |
| 360 | 90 |
| 480 | 97 |
| 600 | 98 |
| 720 | 99 |

TABLE 36

Percent (%) Oxycodone Released per Time in Alcohol and Water Dissolution Medium

| Time (min) | Percent (%) Release Oxycodone HCl |
|---|---|
| 0 | 0 |
| 5 | 0 |
| 15 | 2 |
| 30 | 6 |
| 45 | 9 |
| 60 | 12 |
| 120 | 25 |

TABLE 37

Percent (%) Oxycodone Released per Time in HCl/Water Dissolution Medium after crushing

| Time (min) | Percent (%) Release Oxycodone HCl |
|---|---|
| 0 | 0 |
| 5 | 4 |
| 15 | 15 |
| 30 | 42 |
| 45 | 63 |
| 60 | 78 |
| 120 | 95 |

The data of Table 35 is illustrated in FIG. 9 as the shaded triangles.

Example 16

Using a process similar to that described above in Example 15, again using only 53% of EC for dry mixing with other ingredients, the following formulation was prepared, which differs from Example 15 in the amounts of each component used:

TABLE 38

Granules Formulations

| Ingredient | Amount (% w/w) |
| --- | --- |
| Oxycodone HCl | 46.1 |
| Hydroxypropyl methylcellulose (HPMC) | 36.9 |
| Ethylcellulose | 17.0 |
| Total | 100.00 |

TABLE 39

Coated Granules Formulation

| Ingredient | Amount (% w/w) |
| --- | --- |
| Oxycodone granules (oxycodone HCl, HPMC, ethylcellulose) | 50.0 |
| Ethylcellulose | 33.3 |
| Magnesium stearate | 16.7 |
| Total | 100.00 |

Using a process similar to that described above in Example 15, the following formulation was prepared using different amounts than in Example 15:

TABLE 40

Oxycodone HCl (80 mg) Tablet Formulation

| Component | Amount (% w/w) | Amount (mg) |
| --- | --- | --- |
| Oxycodone coated granules | 40.74 | 346.3 |
| Lactose Monohydrate (fast Flo) | 49.26 | 418.7 |
| COMPRITOL (glyceryl behenate) | 10.00 | 85.0 |
| Total | 100.00 | 850.0 mg |

While COMPRITOL is always kept at 10% of the tablet weight, any change in the actual assay amount, from theoretical values, is accounted for by changing the amount of lactose and coated granules to maintain the amount of Oxycodone HCl at 80 mg. The average tablet weight is 850 mg, and has an average hardness of between 139 and 155 N. The tablet dimensions are 0.3125"×0.5625".

Using a process similar to that of Example 15, the following data was obtained using the above formulation:

TABLE 41

Percent (%) Oxycodone Released per Time in HCl/Water Dissolution Medium

| Time (min) | Percent (%) Release Oxycodone HCl |
| --- | --- |
| 0 | 0 |
| 30 | 5 |
| 60 | 11 |
| 120 | 25 |
| 240 | 52 |
| 360 | 74 |
| 480 | 87 |
| 600 | 94 |
| 720 | 98 |

TABLE 42

Percent (%) Oxycodone Released per Time in Alcohol and Water Dissolution Medium

| Time (min) | Percent (%) Release Oxycodone HCl |
| --- | --- |
| 0 | 0 |
| 5 | 1 |
| 15 | 2 |
| 30 | 6 |
| 45 | 8 |
| 60 | 11 |
| 120 | 23 |

TABLE 43

Percent (%) Oxycodone Released per Time in HCl/Water Dissolution Medium after crushing

| Time (min) | Percent (%) Release Oxycodone HCl |
| --- | --- |
| 0 | 0 |
| 5 | 5 |
| 15 | 13 |
| 30 | 29 |
| 45 | 44 |
| 60 | 57 |
| 120 | 85 |

The data of Table 41 is illustrated in FIG. 9 as the lower curve with shaded squares.

Example 17

Using a process similar to that described above in Example 3, again using only 53% of EC for dry mixing with other ingredients instead of 54%, the following formulation was prepared, which differs from Example 3 in the amounts of each component used and the drug used:

TABLE 44

Granules Formulations

| Ingredient | Amount (% w/w) |
| --- | --- |
| Hydromorphone HCl | 46.6 |
| Hydroxypropyl methylcellulose (HPMC) | 36.4 |
| Ethylcellulose | 17.0 |
| Total | 100.00 |

TABLE 45

| Coated Granules Formulation | |
|---|---|
| Ingredient | Amount (% w/w) |
| Hydromorphone granules | 50.0 |
| Ethylcellulose | 33.3 |
| Magnesium stearate | 16.7 |
| Total | 100.00 |

In this example, Hydromorphone HCl was substituted for Oxycodone HCl. However, the same process steps may be used for various types of API's.

Example 18

Using a process similar to that described above in Example 17, again using only 53% of EC for dry mixing with other ingredients, the following formulation was prepared, which differs from Example 17 in the amounts of each component used:

TABLE 46

| Granules Formulations | |
|---|---|
| Ingredient | Amount (% w/w) |
| Hydromorphone HCl | 46.6 |
| Hydroxypropyl methylcellulose (HPMC) | 36.4 |
| Ethylcellulose | 17.0 |
| Total | 100.00 |

TABLE 47

| Coated Granules Formulation | |
|---|---|
| Ingredient | Amount (% w/w) |
| Hydromorphone granules | 40.0 |
| Ethylcellulose | 40.0 |
| Magnesium stearate | 20.0 |
| Total | 100.00 |

As in Example 17, Hydromorphone HCl replaced Oxycodone HCl as the API.

Example 19

Using a process similar to that described above in Example 18, again using only 53% of EC for dry mixing with other ingredients, the following formulation was prepared, which differs from Example 18 in the amounts of each component used:

TABLE 48

| Granules Formulations | |
|---|---|
| Ingredient | Amount (% w/w) |
| Hydromorphone HCl | 46.6 |
| Hydroxypropyl methylcellulose (HPMC) | 36.4 |
| Ethylcellulose | 17.0 |
| Total | 100.00 |

TABLE 49

| Coated Granules Formulation | |
|---|---|
| Ingredient | Amount (% w/w) |
| Hydromorphone granules | 60.0 |
| Ethylcellulose | 26.7 |
| Magnesium stearate | 13.3 |
| Total | 100.00 |

As in Example 18, Hydromorphone HCl replaced Oxycodone HCl as the API.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A method of making a tablet comprising:
a) combining an opioid with two materials to form a mixture, wherein the first material is ethyl cellulose, and the second material is selected from the group consisting of hydroxypropylmethylcellulose, methylcellulose, hydroxyethylmethylcellulose, sodium carboxy methylcellulose, and hydroxyethylcellulose,
b) granulating the mixture of the opioid and the two materials in the presence of at least one solvent, forming a wet granulate, wherein the at least one solvent is selected from the group consisting of water, C1-C7 alcohols and mixtures thereof, and wherein the wet granulate consists of the at least one solvent, the opioid, the first material and the second material specified in step a);
c) milling and drying the wet granulate formed in step b) to form a granulate comprising an average particle size of about 50 to about 700 microns; wherein the opioid is present in an amount between about 0.1 to about 90 percent by weight of the granulate, the first material defined in step a) is present in an amount between 10 to 75 percent by weight of the granulate, and the second material defined in step a) is present in an amount between 10 to 75 percent by weight of the granulate;
d) depositing a coating on said granulate to produce a coated granulate, wherein the coating is provided in an amount of between about 20 and about 75 percent by weight of the coated granulate, wherein the coated granulate exhibits crush resistance, wherein the coating comprises ethyl cellulose and a fat/wax selected from the group consisting of glycerol behenate, glycerol palmitostearate, stearoyl macroglycerides, carnauba wax, bees wax, microcrystalline wax, and cetyl alcohol, said material deposited on said granulate using an alcohol based solvent;
e) allowing said coated granulate to dry;
f) mixing the dried coated granulate with at least one excipient to form a mixture, wherein the at least one excipient comprises hydroxypropylmethylcellulose; and
g) compressing the mixture to form a tablet.
2. The method according to claim 1, wherein the second material is hydroxypropylmethylcellulose.

3. The method according to claim 1, wherein the hydroxypropylmethylcellulose in step f) is present in an amount of from 2 to 50 percent by weight of the tablet.

4. The method according to claim 1, wherein the at least one excipient further comprises lactose.

5. The method according to claim 4, wherein the lactose is present in an amount of from 10 to 90 percent by weight of the tablet.

6. The method according to claim 5, wherein the lactose is present in an amount of from 10 to 50 percent by weight of the tablet.

* * * * *